United States Patent
Conti et al.

(10) Patent No.: US 8,673,849 B2
(45) Date of Patent: Mar. 18, 2014

(54) LACTADHERIN-DERIVED PEPTIDES AS ANTIVIRAL AGENTS

(75) Inventors: Amedeo Conti, Asti (IT); David Lembo, Turin (IT); Claudio Fabris, Turin (IT); Enrico Bertino, Turin (IT); Santo Landolfo, Turin (IT)

(73) Assignee: ROTALACTIS Srl, Colleretto Giacosa (TO) (IT)

( * ) Notice: Subject to any disclaimer, the term of this patent is extended or adjusted under 35 U.S.C. 154(b) by 0 days.

(21) Appl. No.: 13/701,177

(22) PCT Filed: May 31, 2011

(86) PCT No.: PCT/EP2011/058977
§ 371 (c)(1),
(2), (4) Date: Feb. 5, 2013

(87) PCT Pub. No.: WO2011/151341
PCT Pub. Date: Dec. 8, 2011

(65) Prior Publication Data
US 2013/0130970 A1    May 23, 2013

(30) Foreign Application Priority Data

May 31, 2010  (EP) .................................... 10164496

(51) Int. Cl.
*C07K 7/08* (2006.01)
*C07K 7/06* (2006.01)

(52) U.S. Cl.
CPC ........................................ *C07K 7/08* (2013.01)
USPC ............. 514/3.7; 530/326; 530/328; 530/329

(58) Field of Classification Search
None
See application file for complete search history.

(56) References Cited

U.S. PATENT DOCUMENTS 5,667,797 A    9/1997  Peterson et al.

FOREIGN PATENT DOCUMENTS

EP    2106802 A1    10/2009
WO    2009020405 A1    2/2009

OTHER PUBLICATIONS

DeClercq "Antivirals: Past, present and future" (Mar. 15, 2013) Biochem Pharmacol 85(6): 727-44.*
Davis "Coxsackie Virus" (Aug. 23, 2012) MedicineNet.com http://www.medicinenet.com/coxsackie_virus/article.htm accessed on May 4, 2013.*
Botting et al "Novel approaches to flavivirus drug discovery" (May 2012) Expert Opin Drug Discov. 7(5):417-28.*
Illinois Department of Public Health "Human Metapneumovirus" (Apr. 2009) http://www.idph.state.il.us/public/hb/hb_hMPV.htm downloaded May 5, 2013.*
Van Trieu et al (Abstract in English "Management of acute diarrhea in children" Presse Med (Jan. 2013) 42(1):60-65).*
Holig Peter et al.: "Novel RGD lipopeptides for the targeting of liposomes to integrin-expressing endothelial and melanoma cells", Protein Engineering Design & Selection, vol. 17, No. 5, May 2004, pp. 433-441.
Barello Cristina et al: "Analysis of major proteins and fat fractions associated with mare's milk fat globules", Molecular Nutrition & Food Research, Wiley—VCH Verlag, Weinheim, DE LNKD DOI:10.1002/MNFR.200700311, vol. 52, No. 12, Aug. 22, 2008, pp. 1448-1456.
Kvistgaard A S et al: "Inhibitory effects of human and bovine milk constituents on rotavirus infections", Journal of Dairy Science, American Dairy 1-15 Science Association, US LNKD DOI:10.3168/JDS.S0022-0302(04)73551-1, vol. 87, No. 12, Dec. 1, 2004, pp. 4088-4096.
Conti Amedeo et al: "Proteomics of human milk", Jan. 1, 2007, Proteomics of Human Body Fluids: Principles, Methods, and Applications, Humana Press, US LNKD DOI:10.1007/978-1-59745-432-2 20XP, pp. 437-451, XP009912497, ISBN: 978-1-58829-657-3 p. 443.

* cited by examiner

*Primary Examiner* — Jean C. Witz
*Assistant Examiner* — Mindy Newman
(74) *Attorney, Agent, or Firm* — Rothwell, Figg, Ernst & Manbeck, P.C.

(57) ABSTRACT

The present invention relates to monomeric and multimeric peptidic compounds which have antiviral activity, particularly against integrin-using viruses, more particularly against rotavirus. Further, the present invention refers to compositions comprising said peptidic compounds for medical use or for use as food additives.

44 Claims, 5 Drawing Sheets

Figure 1

```
1  ASGPCFPNPC  QNDGECHVID  DSHRGDVFTQ  YICSCPRGYT
41 GTHCE
```

Figure 2

```
Seq EQ 45    ---------------------------------------------ASGCFPNPCQNDGECH 13
Seq BO       ASGDFCDSSLCLHGGTCLLNEDRTPPFYCLCPEGFTGLLCNETEHGPCFPNPCHNDAECQ 60
Seq HU       ---------------------------------------------LDICSKNPCHNGGLCE 16
                                                          *   ***:*.. *.

Seq EQ 45    VIDDSHRGDVFTQYICSCPRGYTG-HCETTCAMPLGMETG-------------------- 52
Seq BO       VTDDSHRGDVFIQYICKCPLGYVGIHCETTCTSPLGMQTGAIADSQISASSMHLGFMGLQ 120
Seq HU       EISQEVRGDVFPSYTCTCLKGYAGNHCETKCVEPLGMENGNIAN---------------- 60
             .:. *****  .*  *.*   **.* **** *. ****:.*
```

LACTADHERIN-DERIVED PEPTIDES AS ANTIVIRAL AGENTS

CROSS REFERENCE TO RELATED APPLICATION

This application is a 35 U.S.C. 371 National Phase Entry Application from PCT/EP2011/058977, filed May 31, 2011, which claims the benefit of European Patent Application No. 10164496.1 filed on May 31, 2010, the disclosure of which is incorporated herein in its entirety by reference.

REFERENCE TO A SEQUENCE LISTING

The present application includes a Sequence Listing filed in electronic format. The Sequence Listing is entitled "2923-1186_ST25.txt" created on Feb. 4, 2013, and is 9,000 bytes in size. The information in the electronic format of the Sequence Listing is part of the present application and is incorporated herein by reference in its entirety.

DESCRIPTION

The present invention relates to monomeric and multimeric peptidic compounds which have antiviral activity, particularly against integrin-using viruses, more particularly against rotavirus. Further, the present invention refers to compositions comprising said peptidic compounds for medical use or for use as food additives.

Milk is a heterogeneous mixture of different phases in equilibrium with one another: the serum, the suspension of caseins and the fat globule emulsion. The fat globules are generally drops of triglycerides surrounded by a double layer, the typical lipid bilayer, that derives from the apical plasma membrane of the mammary gland epithelial cells, from which they originate. The proteins associated with the membranes of the milk fat globules (milk fat globule membranes, MFGM) fulfil functions that are important for newborns and infants.

Clinical studies (Kurugol et al., 2003; Newburg et al., 1998; Morrow et al., 2004) show that infants not exclusively breast fed have twice the risk of developing gastroenteritis due to rotavirus. These children are fed with various types of preparations depending on the nutritional needs of the newborn or infant. In most cases, these formulas derive from defatted cow's milk fortified with essential fats of vegetable origin. All the proteins associated with the membranes of the milk fat globules (MFGM) are thus excluded from such preparations. Previous studies, which are also the subject of U.S. Pat. No. 5,667,797, show that the biochemical compounds present in human MFGM demonstrate some anti-rotavirus activity. In particular, milk fat globule membranes, substantially free from their lipid portion, are active against rotavirus infection, whereas those same molecules isolated from bovine MFGM do not exhibit such functions. Studies have also shown that purified human lactadherin is active against rotavirus infection whereas the bovine counterpart does not possess this activity (Kvistgaard et al., 2004).

Lactadherin is a glycoprotein present in MFGM, probably associated with the membrane by interaction with the constituent phospholipids. The different lactadherins, isolated from different animal species, are characterised by a certain number of domains: in the N-terminal region these are similar to epidermal growth factor and towards the C-terminal they are homologues of coagulation factors V and VIII. Bovine lactadherin comprises 427 amino acid residues including an N-terminal signal sequence of 18 amino acids, which is cleaved during the intra-cellular processing. The theoretical molecular weight without the signal sequence is approximately 45.6 kDa and the isoelectric point is 6.63. Human lactadherin is a protein of 387 amino acids including an N-terminal signal sequence of 23 amino acids. The theoretical molecular weight without the signal sequence is approximately 40.8 kDa with an isoelectric point of 8.22. When separated by two-dimensional electrophoresis (2DE) these two proteins show an apparent molecular mass above the theoretical value: the difference in weight is explained by the presence of glycosylations.

The rotavirus is a nude RNA virus highly resistant to environmental conditions that is transmitted by the oral and faecal routes. The target cells of this virus are mature apical enterocytes of the villi of the small bowel that, due to the infection, die with consequent atrophy of the villus. The tissue damage induced by the infection causes severe functional alterations of the intestinal mucosa such as loss of electrolytes and reduced water absorption, resulting in acute diarrhoea.

The rotavirus belongs to the type of viruses that exploit integrins as cellular receptor, i.e. rotavirus interact with intergrins for cell attachment and entry. Graham et al. (Journal of Virology, September 2003, p. 9969-9978) disclose studies on viral proteins and sequences which are involved in the interaction with integrins implicated in rotavirus cell attachment and entry. Particular reference is made to the virus-spike proteins VP4, which contains the integrin ligand sequence DGE, which is involved in binding of the integrin-using rotaviruses. The studies are carried out on the integrin ligand peptides DGEA (SEQ ID NO: 19) and GPRP (SEQ ID NO: 24). The authors show that the integrin ligand peptides may inhibit simian rotavirus strain SA11 binding to and infection of MA104 cells in a dose-dependent matter. Zarate et al. (Journal of Virology, October 2004, p. 10839-10847) refer to studies on the rotavirus cell entry and in particular to the establishment of integrin recognition sites which mediate the virus infectivity. Zarate et al., focus their studies on the CNP peptide which was found to be relevant for integrin interaction and infectivity of rotaviruses.

The rotavirus is the most significant cause of severe gastroenteritis in children under the age of five years. The disease is normally self-limiting and without sequelae but a fatal outcome is also possible, associated with dehydration and electrolytic imbalance, chiefly in undernourished children and those with little access to support therapy. No specific anti-rotavirus drugs are currently available, thus severe gastroenteritis is managed through support therapy aimed at reintegrating the lost liquids and correcting the electrolytic and acid-base imbalance. The principal population groups at risk of contracting gastroenteritis due to rotavirus with severe dehydration are children under the age of two years, undernourished and/or immune deficient children and those who are hospitalised and/or in community care.

In this scenario, medical and socio-economic considerations suggest that it would be highly desirable to develop a prophylactic and/or therapeutic preparation based on components from human milk that possess anti-rotavirus activity. On the other hand, it is not possible to use human milk for practical and ethical reasons. Thus, it was an object of the present invention to provide for a pharmaceutically useful compound and preparation exhibiting beneficial effects on rotavirus infection in humans.

Attempts have been made to use bovine milk or components thereof, especially as bovine milk is cheap and readily available in large amounts. However, the respective components from bovine milk do not possess anti-rotavirus activity leading to the conclusion that anti-rotavirus activity is exclusive to human milk (Kvistgaard, supra).

The present inventors surprisingly found that components from equine milk comprising components of membrane associated with equine milk fat globules, and more preferably particularly free from lipid components, exhibit anti-viral activity, particularly against human rotavirus.

In particular, the present inventors found that the equine protein lactadherin extracted from the fat globules of equine milk exhibit the antiviral activity, in particular the anti-rotavirus activity. Finally, the authors of the invention were able to purify and characterise the lactadherin protein of equine milk by determination of the amino acid sequence. FIG. 1 shows the N-terminal domain of the amino acid sequence of the donkey's milk lactadherin (Equus Asinus) which has been determined by the present inventors.

Further, the present inventors have surprisingly found that specific peptide motifs derived from equine lactadherin have anti-viral activity. In particular, these peptide motifs comprise the tripeptide sequences DGE and/or RGD. Without wishing to be bound to any theory, the present inventors have characterised these peptide motifs as able to bind to integrin proteins on the cell surface, thereby specifically inhibiting the binding of integrin-using viruses to the host cell surface, i.e. inhibiting virus attachment to and entry into the host cell. Peptidic compounds comprising one or both of the above tripeptide sequences may be considered integrin ligand peptides, which may compete with the viral proteins for integrin-attachment and thereby inhibiting virus infection by blockade of virus binding and entry into the cell.

Hence, the present invention provides novel anti-viral peptidic compounds and methods for using said peptidic compounds in therapy, e.g. to treat and/or prevent viral diseases, in particular viral diseases caused by integrin-using viruses and even more particularly rotaviruses diseases.

The subject-matter of the present invention is therefore a peptidic compound having a length of up to 50 amino acid residues comprising an amino acid sequence represented by the general formula (I)

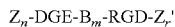  formula (I)

$Z_n$-DGE-$B_m$-RGD-$Z_{r'}'$ or a salt thereof, wherein
each of Z, Z' and B is an amino acid residue, particularly an α-amino carboxylic acid residue,
n is a number from 0 to 12, particularly from 1 to 6 and more particularly from 1 to 2, and
m is a number from 0 to 15, e.g. 0, 1, 2, 3, 4, 5, 6, 7, 8, 9, 10, 11, 12, 13, 14 or 15, particularly from 0 to 12, more particularly from 1 to 10, more particularly from 4 to 10, and even more particularly from 5 to 8, and
r is a number from 0 to 20, particularly from 1 to 12 and more particularly from 1 to 4, and wherein
D is an amino acid residue with an aspartic acid side chain, preferably L-aspartic acid,
G is an amino acid residue with a glycine side chain,
E is an amino acid residue with a glutamic acid side chain, preferably L-glutamic acid, and
R is an amino acid residue with an arginine side chain, particularly L-arginine; and wherein the peptic compound of formula (I) may comprise L- and/or D-amino acid residues, preferably L-amino acid residues.

Further, the subject-matter of the present invention is a peptidic compound having a length of up to 50 amino acid residues comprising an amino acid sequence represented by the general formula (Ia)

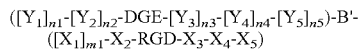  formula (Ia)

$([Y_1]_{n1}$-$[Y_2]_{n2}$-DGE-$[Y_3]_{n3}$-$[Y_4]_{n4}$-$[Y_5]_{n5}$)-B'-$([X_1]_{m1}$-$X_2$-RGD-$X_3$-$X_4$-$X_5$)

or a salt thereof, wherein
$Y_1$, $Y_2$ and $Y_3$ are independently amino acid residues with a neutral polar side chain, preferably with a serine (S), asparagine (N), cysteine (C), glutamine (Q), tyrosine (Y) or threonine (T) side chain,
$Y_4$ is an amino acid residue with a positively charged side chain, preferably with a histidine (H), arginine (R) or lysine (K) side chain,
$Y_5$ is an amino acid residue with a neutral non-polar side chain, preferably with a phenylalanine (F), valine (V), alanine (A), glycine (G), isoleucine (I), leucine (L), methionine (M), proline (P) or tryptophan (W) side chain,
D is an amino acid residue with an aspartic acid side chain, preferably L-aspartic acid,
G is an amino acid residue with a glycine side chain,
E is an amino acid residue with a glutamic acid side chain, preferably L-glutamic acid,
$n_1$, $n_4$ and $n_5$ are independently 0 or 1,
$n_2$ and $n_3$ are 0 or 1, with the provision that at least one of $n_2$ and $n_3$ is 1,
$X_1$ and $X_5$ are independently amino acid residues with a neutral polar side chain, preferably with a serine (S), asparagine (N), cysteine (C), glutamine (Q), tyrosine (Y) or threonine (T) side chain,
$X_2$ is an amino acid residue with a positively charged side chain, preferably with a histidine (H), arginine (R) or lysine (K) side chain,
$X_3$ and $X_4$ are independently amino acid residues with a neutral non-polar side chain, preferably with a phenylalanine (F), valine (V), alanine (A), glycine (G), isoleucine (I), leucine (L), methionine (M), proline (P) or tryptophan (W) side chain,
R is an amino acid residue with an arginine side chain, particularly L-arginine,
G is an amino acid residue with a glycine side chain,
D is an amino acid residue with an aspartic acid side chain, preferably L-aspartic acid, and
$m_1$ is 0 or 1,
and
B' is a covalent chemical bond or a linker group, preferably a peptidic linker group, comprising 1 to 10 amino acid residues, preferably 1 to 5, more preferably 1 to 3 amino acid residues and wherein the peptidic compound of formula Ia may comprise L- and/or D-amino acid residues, preferably L-amino acid residues.

When B' is a covalent chemical bond, this bond is preferably a peptidic bond formed when the carboxyl group of one amino acid residue (e.g. E, $Y_3$, $Y_4$ or $Y_5$) reacts with the amino group of the other amino acid residue (e.g. $X_1$ or $X_2$). Further Examples of covalent chemical bonds are e.g. carboxamide, carbamate, ester, thioester, ether, thioether, tetrazole, thiazole, retroamide and thiamide bonds.

In the context of the present invention, a linker group B' is defined as a bifunctional group, having on both termini a reactive functional end group. With the one reactive end group, the linker reacts to the C-terminus of one amino acid residue of formula (Ia) (e.g. E, $Y_3$, $Y_4$ or $Y_5$). With the other functional group on the other terminus, the linker group binds to the N-terminus of another amino acid residue of formula (Ia) (e.g. $X_1$ or $X_2$).

According to a preferred embodiment of the invention, the linker group is a peptidic linker group comprising 1 to 10, preferably 1 to 5, more preferably 1 to 3 (e.g. 1, 2 or 3) amino acid residues, particularly α-amino carboxylic acid residues. In a very preferred embodiment of the invention, the peptidic linker group comprises 3 amino acid residues, particularly α-amino carboxylic acid residues. In particular, said tripeptidic linker group is preferably represented by the formula (Ib)

$$B_1\text{-}B_2\text{-}B_3 \qquad \text{formula (Ib)}$$

wherein
$B_1$ is an amino acid residue with a neutral non-polar side chain, preferably with a phenylalanine (F), valine (V), alanine (A), glycine (G), isoleucine (I), leucine (L), methionine (M), proline (P) or tryptophan (W) side chain, and $B_2$ and $B_3$ are independently an amino acid residue with a negatively charged side chain, preferably with an aspartic acid (D) or glutamic acid (E) side chain.

In a very preferred embodiment the formula $B_1\text{-}B_2\text{-}B_3$ is represented by

I-D-D wherein
I is an amino acid residue with an isoleucine side chain, preferably L-isoleucine and D is an amino acid residue with an aspartic acid side chain, preferably L-aspartic acid. The amino acid residues of the peptidic linker group may comprise L- and/or D-amino acid residues, preferably L-amino acid residues.

Further suitable linker groups are known to those skilled in the art. Examples of linker groups may include, but are not limited to hetero-, bifunctional small molecules of polymers. Hence, according to another embodiment of the invention, the linker group may be represented by bifunctional $C_6\text{-}C_{12}$ alkyl groups or heterobifunctional $C_6\text{-}C_{12}$ alkyl groups containing from 1 to 3 heteroatoms selected from N, S and O. Alternatively, the linker group may be represented by a bifunctional polymer moiety, preferably a bifunctional oligomer moiety, which is biocompatible, of natural, semi-synthetic or synthetic origin and can have a linear or branched structure. Examples of polymers may include, without limitation, polyalkylene glycols and polyakylene oxides. A very preferred bifunctional polymer moiety is polyethylene glycol (PEG), in particular an intermediary short bifunctional PEG chain, e.g. a bifunctional oligoethylene glycol moiety, e.g. comprising 2-10, preferably 2-8 or 2-6, even more preferably 2, 3 or 4 ethylene glycol monomeric units.

In a further preferred embodiment, the present invention refers to a peptic compound having a length of up to 50 amino acids comprising an amino acid sequence represented by the general formula (II)

$$[Y_1]_{n1}\text{-}[Y_2]_{n2}\text{-}DGE\text{-}[Y_3]_{n3}\text{-}[Y_4]_{n4}\text{-}[Y_5]_{n5} \qquad \text{formula (II)}$$

or a salt thereof, wherein
$Y_1$, $Y_2$ and $Y_3$ are independently amino acid residues with a neutral polar side chain, preferably with a serine (S), asparagine (N), cysteine (C), glutamine (Q), tyrosine (Y) or threonine (T) side chain,
$Y_4$ is an amino acid residue with a positively charged side chain, preferably with a histidine (H), arginine (R) or lysine (K) side chain,
$Y_5$ is an amino acid residue with a neutral non-polar side chain, preferably with a phenylalanine (F), valine (V), alanine (A), glycine (G), isoleucine (I), leucine (L), methionine (M), proline (P) or tryptophan (W) side chain,
D is an amino acid residue with an aspartic acid side chain, preferably L-aspartic acid,
G is an amino acid residue with a glycine side chain,
E is an amino acid residue with a glutamic acid side chain, preferably L-glutamic acid,
$n_1$, $n_4$ and $n_5$ are independently 0 or 1,
$n_2$ and $n_3$ are 0 or 1, with the provision that at least one of $n_2$ and $n_3$ is 1, and wherein the peptidic compound of formula (II) may comprise L- and/or D-amino acid residues, preferably L-amino acid residues.

In a still further preferred embodiment, the present invention further relates to a peptidic compound having a length of up to 50 amino acids comprising an amino acid sequence represented by the general formula (III)

$$[X_1]_{m1}\text{-}X_2\text{-}RGD\text{-}X_3\text{-}X_4\text{-}X_5 \qquad \text{formula (III)}$$

or a salt thereof, wherein
$X_1$ and $X_5$ are independently amino acid residues with a neutral polar side chain, preferably with a serine (S), asparagine (N), cysteine (C), glutamine (Q), tyrosine (Y) or threonine (T) side chain,
$X_2$ is an amino acid residue with a positively charged side chain, preferably with a histidine (H), arginine (R) or lysine (K) side chain,
$X_3$ and $X_4$ are independently amino acid residues with a neutral non-polar side chain, preferably with a phenylalanine (F), valine (V), alanine (A), glycine (G), isoleucine (I), leucine (L), methionine (M), proline (P) or tryptophan (W) side chain,
R is an amino acid residue with an arginine side chain, particularly L-arginine,
G is an amino acid residue with a glycine side chain,
D is an amino acid residue with an aspartic acid side chain, preferably L-aspartic acid, and
$m_1$ is 0 or 1; and wherein the pepticid compound of formula (III) may comprise L- and/or D-amino acid residues, preferably L-amino acid residues.

The peptidic compounds of general formulae (I), (Ia), (II) and/or (III) may comprise L- and/or D-amino acid residue building blocks. The sequences of the peptidic compounds of the invention are written from the N-terminus on the left to the C-terminus on the right.

The present invention refers to peptidic compounds. The term "peptidic compounds" and "peptidic linker" as used herein encompasses compounds, which at least partially comprise amino acid building blocks or analogous thereof, which are linked by covalent bonds, preferably carboxamide bonds. The building blocks are preferably selected from amino-carboxylic acids, e.g. α-amino carboxylic acids or other types of carboxylic acids, e.g. β- or even ω-amino-carboxylic acids. The amino acid building blocks may be selected from genetically encoded L-α-amino-carboxylic acids and/or their D-enantiomers and/or from non-naturally occurring amino acid building blocks. The individual building blocks of the peptidic compounds are linked by covalent bonds, preferably by natural amide bond ("peptidic bond") linkages or other covalent bonds, e.g. carboxamid, carbamate, ester, thioester, ether, thioether, tetrazole, thiazole, retroamide and thioamide bonds.

Subject-matter of the invention are also peptidic compound variants, wherein the simple amino acid building blocks are modified. In particular, said building block modification comprises the substitution of single amino acids, in particular by conservative substitution, wherein an amino acid is replaced with another amino acid of similar chemical structure without altering the functionality of the peptides. Furthermore, according to the invention, also single amino acid modifications may comprise the substitution of single amino acid with amino acid mimetics. Hence, the amino acid building blocks may also be selected from amino acid mimetics. Amino acid mimetics refer to chemical compounds that have a structure that is different from the general chemical structure of an amino acid, but which functions in a manner similar to a naturally occurring amino acid. These non-natural residues are well described in the scientific and patent literature; a few exemplary non-natural residues useful as mimetics of natural amino acid residues and guidelines are described below. Mimetics of aromatic amino acids are, e.g., D- or L-naphthylalanine; D- or L-phenylglycine; D- or L-2-thieneylalanine; D- or L-2,3-, or 4-pyreneylalanine; D- or L-3-thieneylalanine; D- or L-(2-pyridinyl)-alanine; D- or L-(3-pyridinyl)-alanine; D- or L-(2-pyrazinyl)-alanine, D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; D- or L-p-methoxybiphenyl-phenylalanine; D- or L-2-indole(alkyl)alanines; and D- or L-alkylalanines. In this context, the term "alkyl" means a substituted or unsubstituted methyl, ethyl, propyl, hexyl, butyl, pentyl, isopropyl, iso-butyl, sec-isobutyl or iso-penthyl. Aromatic rings of a non-natural amino acid include, e.g., thiazolyl, thiophenyl, pyrazolyl, benzimidazolyl, naphthyl, furanyl, pyrrolyl, and pyridyl aromatic rings.

The peptidic compounds of the invention, as defined above, may therefore include "mimetic" and "peptidomimetic" forms. The terms "mimetic" and "peptidomimetic" refer to a synthetic chemical compound and has substantially the same structural and/or functional characteristics of the peptidic compound of the invention. The mimetic can be either entirely composed of synthetic, non-natural analogues of amino acids, or can either be a chimeric molecule of partially natural amino acids and partially non-natural analogues of amino acids. The mimetic can also incorporate any amount of natural amino acid conservative substitutions as long as such substitutions do not also substantially alter the mimetic's structure and/or activity.

Specific examples of peptidic compounds of formula I and/or formula Ia of the present invention comprise an amino acid sequence selected from

```
                                               (SEQ ID NO: 1)
Q-N-DGE-C-H-V-I-D-D-S-H-RGD-V-F-T-Q
or (SEQ ID NO: 2)
N-DGE-C-H-V-I-D-D-S-H-RGD-V-F-T-Q,
``` wherein the amino acid residues are as defined above. Preferably, the amino acid residues are L-amino acid residues.

With reference to the preferred sequences SEQ ID NO: 1 and SEQ ID NO: 2, Q is an amino acid residue with a glutamine side chain, preferably L-glutamine, N is an amino acid residue with an asparagine side chain, preferably L-asparagine, C is an amino acid residue with a cysteine side chain, H is an amino acid residue with a histidine side chain, preferably L-histidine, V is an amino acid residue with a valine side chain, preferably L-valine, I is an amino acid residue with an isoleucine side chain, preferably L-isoleucine, S is an amino acid residue with a serine side chain, preferably L-serine, F is an amino acid residue with a phenylalanine side chain, preferably L-phenylalanine, T is an amino acid residue with a threonine side chain, preferably L-threonine, and D, G, E and R are as defined above in connection with the peptidic compound of general formula I, i.e. preferably L-aspartic acid, glycine, L-glutamic acid and L-arginine, respectively.

Further preferred examples of peptidic compounds of formula I and/or formula Ia comprise an amino acid sequence of SEQ ID NO: 1 or SEQ ID NO: 2, wherein
Q may be substituted with an amino acid residue with another neutral polar side chain, e.g. with N, C, S, Y or T;
N may be substituted with an amino acid residue with another neutral polar side chain, e.g. with Q, C, S, Y or T;
C may be substituted with an amino acid residue with another neutral polar side chain, e.g. with N, T, Q, Y or S;
H may be substituted with an amino acid residue with another positively charged side chain, e.g. with R or K;
V may be substituted with an amino acid residue with another neutral non-polar side chain, e.g. with A, F, G, I, L, M, P or W;
I may be substituted with an amino acid residue with another neutral non-polar side chain, e.g. with A, F, G, V, L, M, P or W;
S may be substituted with an amino acid residue with another neutral polar side chain, e.g. with N, C, Q, Y or T;
F may be substituted with an amino acid residue with another neutral non-polar side chain, e.g. with A, V, G, I, L, M, P or W;
T may be substituted with an amino acid residue with another neutral polar side chain, e.g. with N, C, Q, Y or S;
and
D may be substituted with an amino acid residue with another negatively charged side chain, e.g. E, with the provision that the amino acid residue D of the tripeptides DGE and RGD is an amino acid residue with an aspartic acid side chain, preferably L-aspartic acid.

Further preferred examples of peptidic compounds of formula I and/or formula Ia comprise an amino acid residue selected from:

```
                                               (SEQ ID NO: 7)
N-N-DGE-C-H-V-I-D-D-S-H-RGD-V-F-T-Q (SEQ ID NO: 8)
Q-N-DGE-C-H-V-I-D-D-S-H-RGD-V-F-S-Q
or (SEQ ID NO: 9)
Q-N-DGE-C-H-V-I-D-D-S-H-RGD-V-F-Q-T.
```

Specific examples of peptidic compounds of formula II of the present invention comprise an amino acid sequence selected from:

```
                                               (SEQ ID NO: 3)
Q-N-DGE-C-H-V
or (SEQ ID NO: 4)
N-DGE-C-H-V,
``` wherein the amino acid residues are as defined above. Preferably, the amino acid residues are L-amino acid residues.

With reference to the preferred sequences SEQ ID NO: 3 and SEQ ID NO: 4, Q is an amino acid residue with a glutamine side chain, preferably L-glutamine, N is an amino acid residue with an asparagine side chain, preferably L-asparagine, C is an amino acid residue with a cysteine side chain, preferably L-cysteine, H is an amino acid residue with a histidine side chain, preferably L-histidine, V is an amino acid residue with a valine side chain, preferably L-valine and D, G and E are as defined above in connection with the peptidic compound of general formula II, i.e. preferably L-aspartic acid, glycine and L-glutamic acid, respectively.

Specific examples of the peptidic compound of formula III of the present invention comprises an amino acid sequence selected from

```
                                               (SEQ ID NO: 5)
S-H-RGD-V-F-T
or
```

-continued

H-RGD-V-F-T, (SEQ ID NO: 6)

wherein the amino acid residues are as defined above. Preferably, the amino acid residues are L-amino acid residues.

With reference to the preferred sequences SEQ ID NO: 5 and SEQ ID NO: 6, S represents an amino acid residue with a serine side chain, preferably L-serine, H represents an amino acid residue with an histidine side chain, preferably L-histidine, V represents an amino acid residue with a valine side chain, preferably L-valine, F represents an amino acid residue with a phenylalanine side chain, preferably L-phenylalanine, and T represents an amino acid residue with a threonine side chain, preferably L-threonine, and R, G and D are as defined above in connection with the peptidic compound of general formula III, i.e. preferably L-arginine, glycine and L-aspartic acid, respectively.

The peptidic compounds of the present invention may be linear or cyclic peptides. The monomeric peptide compounds of the present invention may have a length of up to 50 amino acid residues, preferably a length of up to 45, 30, 35, 20 or 15 amino acids. In particular, the peptidic compounds of general formula I may have preferably a length of from at least 6, 7, 8, 9, 10, 11, 12, 13, 14, 15, 16, 17, 18, 19 or 20 amino acid residues, preferably of at least 19 or 20 amino acid residues. The peptidic compounds of formula Ia may have preferably a length of from at least 11, 12, 13, 14, 15, 16, 17, 18, 19 or 20, preferably of a least 16, 17, 18, 19 or 20, very preferably of at least 19 or 20 amino acid residues. The peptidic compounds of formula II may have a lengths of from at least 4, 5, 6, 7, 8 or 10 amino acid residues, preferably of at least 5, 7 or 8 amino acid residues. Finally, the peptidic compounds of formula III may have a length of at least 7, 8, 10 or 12 amino acid residues, preferably of at least 7 or 8 amino acid residues.

A further preferred embodiment of the present invention refers to a peptidic compound as described above, e.g. a peptidic compound of general formula I, Ia, II and/or III in combination with a further active agent, preferably a further antiviral active agent. Preferably, the further active agent is a further antiviral peptidic compound, i.e. a further peptidic compound of formula I, Ia, II and/or III. Consequently, a preferred embodiment of the present invention comprises a combination of any one of the peptidic compounds of formula I, Ia, II and/or III. In a very preferred embodiment, the present invention is directed to a combination of the peptidic compound of formula II, comprising the active tripeptide DGE, and the peptidic compound of formula III, comprising the active tripeptide RGD. Specific examples of such a combination is represented by a combination of the peptidic compounds of SEQ ID NO: 3 and/or SEQ ID NO: 4 with peptidic compounds of SEQ ID NO: 5 and/or SEQ ID NO: 6.

In a further embodiment the peptidic compounds of the present invention may be used in combination with probiotic microorganisms, which are active in the gastrointestinal tract. In particular, these probiotic microorganisms are viable microbials which beneficially influence the host by colonization of the gastrointestinal tract, in particular the gut, and improving, stimulating and stabilizing the intestinal microbial flora balance. The probiotic microorganism may be selected from bacteria, yeasts and/or bacilli, preferably from bacteria, more preferably from lactic acid bacteria. Examples of suitable lactic acid bacteria include *Lactobacillus* (e.g., *Lactobacillus casei, Lactobacillus paracasei, Lactobacillus rhamnosus* and *Lactobacillus reutarii*), *Bifidobacteria, Lactococcus* (e.g., *Lactococcus lactis*) and *Streptococcus*.

According to one preferred embodiment of the present invention, the peptidic compound of formula I, Ia, II and/or III are peptidic compounds derived from the naturally occurring amino acid sequence portion of equine lactadherin, particularly of horse and donkey lactadherin. Said equine lactadherin may be isolated from biological material, e.g. from equine milk. Based on the sequence portion of the naturally occurring equine lactadherin sequence a specific embodiment of the present invention refers to a peptidic compound of formula (I), wherein (a) B is (i) the amino acid sequence

CHVIDDSH, wherein
the amino acid residues are as defined above, preferably L-amino acid residues,
(ii) an amino acid sequence having an identity degree of at least 50%, particularly 75%, thereto, or
(iii) an amino acid sequence having at least 4 contiguous amino acids of (i)
(b') Z is (i) the amino acid sequence

ASGPCFPNPCQN, wherein the amino acid residues are as defined above, preferably L-amino acid residues,
(ii) an amino acid sequence having an identity degree of at least 50%, particularly 75%, thereto, or
(iii) an amino acid sequence having at least 2, preferably at least 4 contiguous amino acids of (i), and/or
(c') Z' is (i) the amino acid sequence

VFTQYICSC PRG YTGTHCE wherein the amino acids are as defined above, preferably L-amino acid residues,
(ii) an amino acid sequence having an identity degree of at least 50%, particularly 75%, thereto, or
(iii) an amino acid sequence having at least 4 contiguous amino acids of (i).

Alternatively, the peptidic compounds of the invention may be obtained by peptide synthesis, e.g. by peptide synthesis carried out in solid phase by Fmoc/tBu chemistry. Further alternatively, the peptide compounds of the invention may be produced recombinantly in any suitable host, e.g. in a prokaryotic cell or in an eukaryotic cell or a non-human organism transformed or transfected with a nucleic acid molecule coding for the peptidic compound of the invention, in particular comprising the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 or SEQ ID NO: 9. Said nucleic acid molecule may be transferred to the host as a component of a vector or any suitable vehicle.

In a further embodiment, the present invention refers to a multimeric compound comprising as units a plurality of peptidic compounds as described above, e.g. the peptidic compounds of formula I, Ia, II and/or III, wherein the individual peptidic compounds units are covalently linked, e.g. by covalent bonds or by multifunctional, e.g. di- or trifunctional moieties, such as di- or trifunctional amino acids. The individual monomeric peptidic units in the multimeric compound may be the same or different.

For example, a multimeric compound of the present invention may comprise 2, 3, 4, 5, 6, 7, 8 copies or more of the peptidic compounds, e.g. the compounds of formula I, Ia, II and/or III. The multimeric compound may comprise the peptidic compounds multimerised on a matrix, e.g. a matrix based on a polypeptide, a mono-, oligo- or polysaccharide or an organic polymer, preferably a linear organic polymer. For example, the matrix may be selected from poly(N-alkyl (meth)acrylamid), poly(N,N-dialkyl(meth)acrylamid), polymelamin, dextrane, cyclodextrine, polyethyleneglycol and/or polyvinylpyrrolidone. The coupling of the peptidic compounds to the matrix preferably occurs via the N- and/or C-termini of the peptidic compound, e.g. using homo- and/or hetero-bifunctional linkers which allow coupling to reactive groups, e.g. hydroxy-, amino-, thiol- or carboxyl groups on the matrix.

The multimeric compound of the invention has either a linear or a branched, particularly a dendritic structure.

In a further embodiment, the multimeric compound is selected from:

(i) $P_c$-$(J^1$-$P_c)_m$-$J^1$-$(P_c)_{m'}$ (IVa)

wherein $P_c$ is a peptidic compound of formulae I, Ia, II or III as defined above, $J^1$ is a covalent bond or a bifunctional linker, e.g. a dialcohol such as propylene glycol, a dicarboxylic acid such as succinic acid, a diamine such as ethylene diamine, an amino acid, a hydroxy carboxylic acid, e.g. a hydroxy alconoic acid, or a diisocyanate, and m is 0 or a positive whole number, and m' is 0 or 1,

(ii) $[[P_c)_{n1}J^{1'}]_{n2}]J^2$ (IVb)

wherein $P_c$ is a peptidic compound of formulae I, Ia, II or III as defined above, $J^{1'}$ is in each case independently a linker having a functionality of at least 3, e.g. a trifunctional amino acid such as lysine, ornithine, nor-lysine, aminoalanine, aspartic acid or glutamic acid, and
$J^2$ is a linker having a functionality of at least 2, and
$n_1$ and $n_2$ in each case independently are a whole number of at least 2, preferably 2, 3 or 4, more preferably 2,

(iii) $\{[[(P_c)_{n1}J^{1'}]_{n2}J^{2'}\}_{n3}J^3$ (IVc)

wherein $P_c$ is a peptidic compound of formulae I, Ia, II or III as defined above, $J^{1'}$ and $J^{2'}$ are in each case independent linkers having a functionality of at least 3, e.g. a trifunctional amino acid such as lysine, ornithine, nor-lysine, aminoalanine, aspartic acid or glutamic acid,
$J^3$ is a linker having a functionality of at least 2 and
$n_1$, $n_2$ and $n_3$ are in each case independently whole numbers of at least 2, preferably 2, 3 or 4, more preferably 2.

The multimeric compound (IVa) is a multimeric linear compound, wherein a plurality of peptidic compounds are connected via covalent bonds and/or homo- or hetero-bifunctional linkers $J^1$. Preferably, the multimeric compound comprises up to 3, more preferably up to 4, 5, 6, 7 or 8 units of peptidic compounds of formula I, Ia, II and/or III. In a very preferred embodiment, the multimeric linear compound of formula (IVa) comprises 5 units of peptidic compounds of the invention connected via covalent bonds, in particular via natural amide bonds ("peptidic bonds"). The pentameric multimeric linear compound preferably comprises 5 units of the peptidic compounds of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 or SEQ ID NO: 9 or a combination thereof. Thus, according to this preferred embodiment of the invention, the multimeric compound (IVa) has the structure $P_c$-$(J^1$-$P_c)_3$-$J^1$-$(P_c)_1$, wherein $P_c$ is a peptidic compound selected from SEQ ID NO: 1 to 9, preferably SEQ ID NO: 1, 2, 7, 8 or 9 and $J^1$ is a covalent bond, preferably a peptidic bond.

The multimeric compounds (IVb) and (IVc) are branched compounds, wherein individual peptidic units $P_c$ are connected via linkers having a functionality of at least three. In a further embodiment, the multimeric compound (IVb) comprises four peptidic units and has the structure:

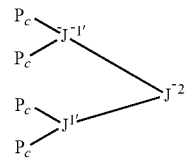

In a further preferred embodiment, the multimeric compound (IVc) comprises eight peptidic units $P_c$ and has the structure:

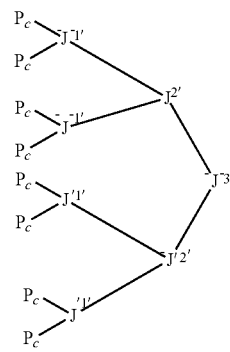

The linker moiety $J^2$ of the multimeric compound (IVb) and the linker moiety $J^3$ of the multimeric compound (IVc) may be preferably a linker having a functionality of 3, preferably a tri-functional amino acid linker, most preferably a lysine. In a still preferred embodiment, the linkers $J^2$ and $J^3$ are bond at the C-terminal to further amino acid residues, preferably to 1, 2, 3 or 4 amino acid residues, which may be selected from α-, β- or even ω-amino acid residues. In a very preferred embodiment, the further amino acid residue bond to the C-terminal of $J^2$ and/or $J^3$ linker is a β-amino acid residue, most preferably a β-alanine residue.

In a preferred embodiment of the invention, the multimeric compound (IVb) has the structure

$[[(P_c)_2Lys]_2]Lys$-β-Ala (V)

or

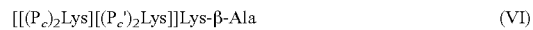

$[[(P_c)_2Lys][(P_c')_2Lys]]Lys$-β-Ala (VI)

Specific examples of multimeric peptidic compounds according to the present invention comprise a monomeric peptidic compound unit as described above or a combination thereof, preferably an amino acid sequence as defined in SEQ ID NO: 1 to 9 or a combination thereof. A very preferred example of a multimeric peptidic compound according to the invention, in particular of a multimeric compound (VI), is represented by the structure:

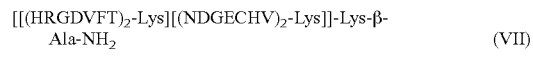

$[[(HRGDVFT)_2$-$Lys][(NDGECHV)_2$-$Lys]]$-$Lys$-β-Ala-$NH_2$ (VII)

wherein β-Ala is a naturally occurring β-alanine amino acid residue, in which the amino group is at the β-position from the carboxylate group residue and wherein the cysteine residue of the peptidic monomeric compound unit has an optionally modified side chain, e.g. a methylated side chain.

A further preferred embodiment of the invention refers to the multimeric peptidic compounds as described above, in particular the compounds of formulae (IVa), (IVb) and/or (IVc) in combination with a further active agent, in particular a further antiviral agent. Preferred example is the combination with a further antiviral monomeric peptidic compound of the invention or a further antiviral multimeric compound of the invention. Further, the multimeric peptidic compounds may be used in combination with probiotic microorganisms as described above.

In a still further embodiment, the compounds of the present invention, i.e. the monomeric peptidic compounds I, Ia, II and III and the multimeric compounds IVa, IVb and IVc, comprise at least one modification, particularly selected from a lipid, amid, ester, acyl and/or alkyl moiety attached thereto, e.g. attached to an N-terminal group, a C-terminal group and/or a side chain group. Preferably, the modified monomeric or multimeric peptidic compounds are N-terminally and/or C-terminally modified peptidic compounds.

Hence, the present invention also relates to derivatives of the monomeric and multimeric peptidic compounds obtained from at least one modification, in particular peptidic derivatives selected from amidated, acetylated, sulfated, lipidated, phosphorylated, glycosylated, oxidized or polyethylene glycol-modified derivates. An especially preferred modification is the attachment of acetyl, e.g. acetyl groups to the N-terminus and/or the amidation of free C-terminus.

Specifically, a preferred modified monomeric and/or multimeric peptidic compound comprises a protected amino acid residue with a glutamine side chain, particularly a protected L-glutamine, at the N-terminal group. This modification enhances stability of the compounds of the present invention comprising an N-terminal amino acid residue with a glutamine side chain. Preferred examples of such modification is a glutamine residue, wherein the N-terminal amino acid and/or the carboxyl side chain group is protected, e.g. by acyl, such as acetyl groups, amino groups etc. More preferably, the N-terminal amino acid group of the glutamine amino acid residue is protected by acetylation. As specific examples, in the peptidic compounds of SEQ ID NO: 1, 3, 8 and 9 the glutamine amino acid residue at the N-terminus may be modified by acetylation.

A further preferred modification of the peptidic compounds of the present invention comprises the introduction of a protecting group on the side chain of an amino acid residue with a cystein side chain, preferably a protected L-cystein. A preferred example of such a modification is the protection of the cystein side chain by methylation. This modification prevents disulfide bonds formation and aggregation of the peptidic compounds. As specific examples, the side chain of cystein amino acid residues of the peptidic compounds of SEQ ID NO: 1, 2, 3, 4, 7, 8 and 9 may be modified by methylation.

A further embodiment of the invention relates to genetically engineered microorganisms able to produce the peptidic compounds of the present invention. Preferably, the microorganism is transferred with an expression vector comprising the nucleic acid molecule coding for the peptidic compound of the invention. E.g. the expression vector may contain a constitutive promoter in order to express the peptidic compounds of the invention. Alternatively, the promoter may be chosen to be active for specific expression only, e.g. suitable for GIT specific expression only.

In particular, this aspect of the invention refers to a method for the production of the peptidic compounds of the invention and at the same time to a method for administration and delivery of the peptidic compounds of the invention. In particular, this method may be useful for delivery of the peptidic compound to the mucosal surface of the gastro-intestinal tract (GIT). This will enable an in vivo production and release of the peptidic compounds, preferably over a prolonged period of time, whereby the compounds of the invention may exploit their antiviral, in particular anti-rotavirus activity, directly in situ against the enteropathogenic viruses, particularly rotaviruses.

The expression of the peptidic compounds in microorganisms provides an effective and cost-efficient production system, since large quantities of peptidic compounds may be synthesized and secreted. Further, the transformed microorganisms are of good wide scale applications, since they require minimal handling and storage costs.

On the other hand, this aspect of the invention also represents an efficient delivery system for the peptidic compounds to the gastro-intestinal-tract (GIT), wherein the peptidic compounds may directly combat the enteropathogenic virus, in particular the rotavirus. Moreover, the present aspect of the invention has the advantage that the in vivo production of the peptidic compounds locally in the GIT circumvents the problem of degradation of orally administered peptides in the stomach. The microorganisms will remain in the gut and enable the constant production of the peptidic compound, i.e. enable more prolonged and constant protection against the enteropathogenic virus, in particular the rotavirus. Furthermore, the microorganisms themselves may have the ability to undergo transient colonization of the GIT and, hence, to stabilize and reinforce the enteromucosal barrier.

Preferably, the microorganism may be probiotic microorganism. Examples of suitable probiotic microorganism include lactic acid bacteria. More preferably, the microorganism is chosen from the *Lactobacillus* genus, the *Lactococcus* genus, the *Bifidobacterium* genus or the *Streptococcus* genus. Examples of *Lactobacillus* include *Lactobacillus casei, Lactobacillus paracasei, Lactobacillus rhamnosus* and *Lactobacillus reutarii*. An example of a *Lactococcus* is *Lactococcus lactis*.

The monomeric and/or multimeric peptidic compounds of the present invention are for use as medicament. In fact, the peptidic compounds of the present invention may have antiviral activity. In particular, the peptidic compounds of the invention exhibit a significant antiviral activity against integrin-using viruses. Preferably, the antiviral peptidic compounds of the invention can inactivate the viruses before they enter into the cells, by preventing the attachment and/or adsorption of the virus to the target cell. Hence, the compounds of the present invention is used as a medicament for the prevention and/or treatment of viral infections, particularly of infections caused by viruses that exploit integrins as cellular receptor ("integrin-using viruses"). Examples of integrin-using viruses are rotavirus, herpes virus, coxsackie virus, metapneumovirus, West Nile virus, and/or foot-and-mouth disease virus, particularly rotavirus. Hence, the compounds of the present invention are used for the prevention and/or treatment of infections caused by the above virus, preferably by rotavirus.

A further subject-matter of the present invention is a composition for medical use comprising at least one compound as defined above, e.g. a monomeric peptidic compound of formula I, Ia, II or III or a multimeric peptidic compound of formula IVa, IVb or IVc as defined above or a combination thereof, together with pharmaceutical acceptable carriers, diluents and/or adjuvants. Preferably, the composition may comprise one or more additional active agents as described above. To prepare the pharmaceutical composition, the peptidic compounds of the invention are synthesized or otherwise obtained, purified as necessary or desired, and then preferably lyophilized and stabilized. The peptide can then be adjusted to the suitable concentration and optionally combined with other pharmaceutical acceptable agents.

For use in human or veterinary medicine, the composition is preferably in form of a pharmaceutical dosage form selected from solids, liquids or gels and combinations thereof. Preferably, the composition for medical use is for oral administration in liquid or in solid form, e.g. in powdered form. It is preferred that the composition of the invention is in powdered form.

The peptides of the invention as well as the composition of the invention is particularly suitable for oral administration, since they are advantageously not susceptible to digest enzyme degradation, in particular to trypsin digestion. In particular the peptides of the invention do maintain their antiviral activity in vitro even in the presence of digestive enzymes, in particular in the presence of trypsin. The digestive enzyme trypsin usually cleaves peptides and proteins after arginine residues (R). However, the present inventors could successfully show that the peptides of the invention are not susceptible to trypsin digestion (Examples 2 and 4b).

The pharmaceutical dosage form comprises an amount of the active agent, i.e. the monomeric or multimeric peptidic compound as defined above, which is effective for the treatment and/or prevention of infection caused by, associated with or accompanied by the presence of the pathogenic integrin-using virus. The actual amount of the active agent may vary depending on the administration route and the type and severity of disorder to be treated. To achieve the desired effect(s), the peptidic monomeric or multimeric compound may be administered as single or divided dosage, for example of at least about 0.05 to about 5 mg/kg body weight/die, preferably about 1 mg/kg body weight/die, although other dosages may provide beneficial results.

In another particularly preferred embodiment, the invention provides a composition for use as a dietary supplement, in particular as food supplement comprising at least one compound as defined above, e.g. a peptidic compound of formula I, Ia, II and III or a multimeric compound of formula IVa, IVb or IVc as defined above or a combination thereof. The term "dietary/food supplement" as used herein encompasses any food supplement product which can be suitable for being supplemented to, e.g. mixed in, dissolved in or springeled on any food product for human and animal use. In a particularly preferred embodiment, the food supplement is a powder that has to be dissolved in a beverage or mixed in a solid food product.

A composition, administered in the form of a dietary/food supplement, would have no contra-indications, since of natural origin, and would readily be accepted by the consumer. Said food supplement is especially suitable as an additive for formulas for the nutrition of children, in particular children under the age of two years, or under-nourished or immunodeficient children or children who are hospitalised and/or in community care, as well as for children with little access to support therapy. Thus, it is preferred to administer any of the inventive compounds and compositions to children and/or newborns. Based on the natural origin of the inventive products, the acceptability for both parents and children would be even more readily.

It is preferred that the composition for use as food additive is in powdered form, in particular as additive for children and/or newborns food additive, e.g. powdered milk. The powdered form is characterised by a number of advantages such as easier handling, excellent storage stability as well as a wide range of possible applications, e.g. as a dietary supplement which may be dissolved in any suitable liquid or which may be mixed with any suitable dried component.

The present invention shall be illustrated further by the following Examples and Figures.

DESCRIPTION OF THE FIGURES

FIG. 1:
N-terminal domain comprising the first 45 amino acids of the amino acid sequence of lactadherin of *Equus asinus*;
FIG. 2:
Amino acid sequence alignment of N-terminal domains of equine (EQ45), bovine (BO) and human (HU) lactadherin.

EXAMPLES

Example 1

Production of Rotavirus and Viral Titration

Figure 3:
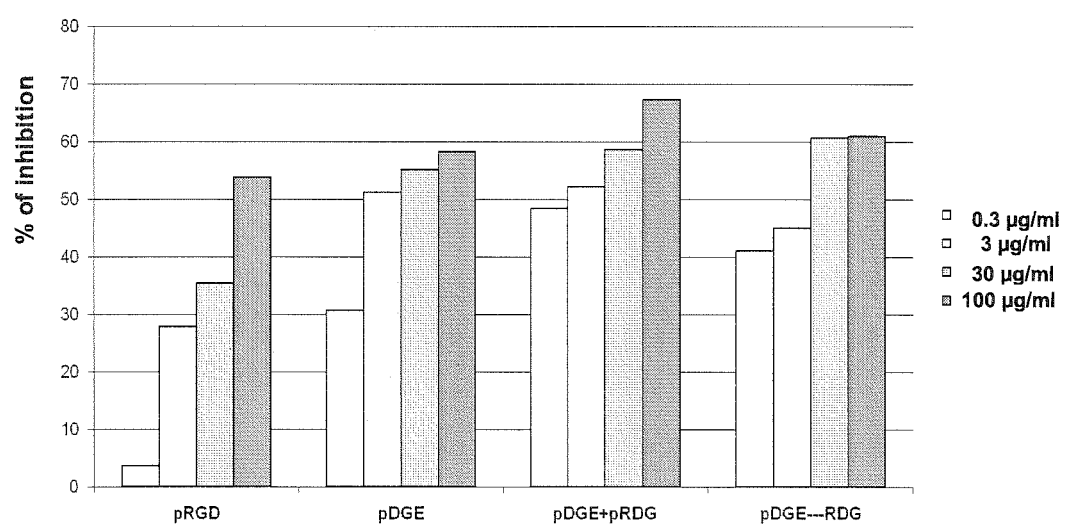
FIG. 3:
Inhibiting activity of the peptidic compound of the invention and combination thereof versus human rotaviruses.

To cultivate the rotavirus, the cell line MA-104 (monkey foetal kidney cells), obtained from the Cell Substrata Centre of the Experimental Animal Disease Institute, Brescia, Italy, was used. This cell line is cultured as a monolayer in EAGLE minimum essential medium (MEM) containing 5% heat-inactivated (56° C. for 30 minutes) bovine foetal serum (Sigma) and is maintained at 37° C. at 5% $CO_2$.

For the in vitro infection assay, the cell line MA-104 and the human rotavirus strain Wa (TC adapted), obtained from the American Type Culture Collection (ATCC VR-2018) and propagated in MA-104 cells, were used.

For viral production, the virus was pre-activated with 8 μg/ml of tripsin (Sigma) (viral stock tripsin ratio 1:1) for 45 minutes at 37° C., diluted×10 in medium, then inoculated onto the monolayer of MA-104 cells (100% confluence) at a multiplicity of infection (MOI) equal to 5 pfu/cell. After 60-90 minutes at 37° C., the inoculum was removed and the monolayer washed with PBS and incubated at 37° C. in serum-free medium containing 0.5-1 μg/ml of tripsin.

When a complete cytopathic effect (CPE) was observed (after approx. 2-7 days) the infected culture was frozen and thawed three times, centrifuged (3,000×g, 10 minutes) and the supernatant stored at −70° C. The viral titre was determined by the standard $TCID_{50}$ method and expressed as $TCID_{50}$/ml and, after appropriate conversion, as plaque-forming units/ml (PFU/ml).

Example 2

Evaluation of the Antiviral Activity of the Peptidic Compounds of the Invention by Immunocytochemistry To set up the assay, cells were seeded in 96-well plates and, once 80% confluence was achieved, were pre-treated for 1 hour with increasing concentrations of RGD- and/or DGE-containing peptides or their mutated counterparts and incubated at 37° C. The peptides containing the RGD or the DGE motif were used either alone or in combination. Cells were then washed with medium and infected with the pre-activated virus (5 µg/ml tripsin for 30 minutes at 37° C.) in the presence of the peptides. After a 1 hour incubation cells were washed with medium and incubated in medium containing 0.5 µg/ml tripsin and the peptides at 37° C. for 20 hours. The infected cells were visualised through an immunoperoxidase assay, using murine monoclonal antibodies specific for the capsidic protein VP6 of the rotavirus (Abcam) and the kit "UltraTech HRP Streptavidin-Biotin detection system" (Beckman Coulter). The infected cells were counted by observation under the optical microscope and the percentage of infection calculated by comparison of treated with non-treated cells.

The peptides used were the following:
1. Peptidic compounds of the invention

```
SEQ ID NO: 5:
S-H-R-G-D-V-F-T

SEQ ID NO: 3:
Q-N-D-G-E-C-H-V

SEQ ID NO: 1:
Q-N-D-G-E-C-H-V-I-D-D-S-H-R-G-D-V-F-T-Q
```

2. Mutated peptidic compounds

```
                                    (SEQ ID NO: 15)
pRGE: S-H-R-G-E-V-F-T (RGD -> RGE mutation)

(SEQ ID NO: 16)
pAGE: Q-N-A-G-E-C-H-V (DGE -> AGE mutation)
```

3. Peptidic compounds derived from bovine lactadherin sequence

```
                                    (SEQ ID NO: 17)
Bo-RGD: S-H-R-G-D-V-F-I
```

4. Peptidic compounds derived from human lactadherin sequence:

```
                                    (SEQ ID NO: 18)
Hu-RGD: E-V-R-G-D-V-F-P
```

5. Control peptide (Graham et al.):

```
                                    (SEQ ID NO: 19)
D-G-E-A
```

The median results of several experiments testing the anti-rotavirus activity of the lactadherin-derived peptides of the invention compared with the mutated and/or control peptides are shown in the following table 1:

TABLE 1

| PEPTIDE | IC$_{50}$ (µM) | IC$_{50}$ (µg/ml) |
|---|---|---|
| SEQ ID NO: 5 | 110.6 | 101.5 |
| Bo-RGD | 394.8 | 367.1 |
| Hu-RGD | 103.8 | 95.3 |
| SEQ ID NO: 3 | 17.3 | 15.6 |
| SEQ ID NO: 1 | 1.72 | 3.9 |
| DGEA | 311.2 | 121.4 |
| pRGE | 599.9 | 558.5 |
| pAGE | 256.6 | 219.6 |

Further, in the following tables 2-5, results of one representative experiment are shown. In particular, the antiviral activity of the peptidic compounds of the invention alone and the antiviral activity of a combination of said peptidic compounds was tested. Tables 2 and 3 show the antiviral activity of the peptidic compounds comprising the RGD-motif (SEQ ID NO: 5) and the DGE-motif (SEQ ID NO: 3), respectively. Table 4 shows the antiviral activity of a combination of said peptidic compounds (SEQ ID NO: 5 and SEQ ID NO: 3). Table 5 shows the results of the peptidic compound of the invention comprising both the RGD- and DGE-motif (SEQ ID NO: 1).

TABLE 2

| SEQ ID NO: 5 | Molarity × 10$^{-6}$ (µM) | % of inhibition |
|---|---|---|
| 0.3 µg/ml | 0.28 | 3.65 |
| 3 µg/ml | 2.8 | 22.27 |
| 30 µg/ml | 28 | 34.21 |
| 100 µg/ml | 93.3 | 46.93 |

TABLE 3

| SEQ ID NO: 3 | Molarity × 10$^{-6}$ (µM) | % of inhibition |
|---|---|---|
| 0.3 µg/ml | 0.29 | 30.72 |
| 3 µg/ml | 2.9 | 35.34 |
| 30 µg/ml | 29 | 47.56 |
| 100 µg/ml | 96.6 | 52.68 |

TABLE 4

| SEQ ID NO: 5 + SEQ ID NO: 3 | Molarity × 10$^{-6}$ (µM) | % of inhibition |
|---|---|---|
| 0.3 µg/ml | 0.15 | 48.42 |
| 3 µg/ml | 1.5 | 54.38 |
| 30 µg/ml | 15 | 55.45 |
| 100 µg/ml | 50 | 61.42 |

TABLE 5

| SEQ ID NO: 1 | Molarity × 10$^{-6}$ (µM) | % of inhibition |
|---|---|---|
| 0.3 µg/ml | 0.11 | 41.17 |
| 3 µg/ml | 1.1 | 45.08 |
| 30 µg/ml | 11 | 60.78 |
| 100 µg/ml | 36.6 | 60.99 |

The results of the above representative experiments are further summarised in FIG. 3.

Further anti-rotavirus activity tests as described above have been conducted to test the antiviral activity of the peptidic compounds of the invention SEQ ID NO: 7, SEQ ID NO: 8 and SEQ ID NO: 9 as reported in Table 6. All peptides show antiviral activity. Moreover, the peptidic compound SEQ ID NO: 10 was obtained, in which a modification has been introduced in both of the DGE-motif and RGD-motif. In particular the DGE-motif has been modified to the AGE triplet and the RGD-motif has been modified to the RGE triplet (SEQ ID NO: 10). As shown in Table 6, such peptide has completely lost any anti-rotavirus activity. Finally, the inventors have synthesized the peptide of SEQ ID NO: 11. In SEQ ID NO: 11, the amino acid residue $X_2$ according to formula Ia (an amino acid residue with a positively charged polar side chain, preferably with a histidine side chain (H)) has been modified to an amino acid residue with an aspartic acid side chain (D).

The aim was to evaluate whether the peptides of the invention are susceptible to trypsin digestion due to the presence of an arginine residue (R) that is known to be protected by an aspartic acid residue (D) at its N-terminal side. The results in Table 6 show that the peptide of SEQ ID NO: 11 maintains its anti-rotavirus activity in spite of the presence of a theoretical bond for trypsin cleavage.

SEQ ID NO: 7:
NNDGECHVIDDSHRGDVFTQ

SEQ ID NO: 8:
QNDGECHVIDDSHRGDVFSQ

SEQ ID NO: 9:
QNDGECHVIDDSHRGDVFQT

SEQ ID NO: 10:
QNAGECHVIDDSHRGEVFTQ
(DGE -> AGE mutation, RGD -> RGE mutation)

SEQ ID NO: 11:
QNDGECHVIDDSDRGDVFTQ

TABLE 6

| Peptide | IC$_{50}$ (µM) | IC$_{50}$ (µg/ml) |
|---|---|---|
| SEQ ID NO: 7 | 13.51 | 30.51 |
| SEQ ID NO: 8 | 6.35 | 14.43 |
| SEQ ID NO: 9 | 4.169 | 9.469 |
| SEQ ID NO: 10 | >220 | >500 |
| SEQ ID NO: 11 | 10.52 | 23.90 |

Example 3

Evaluation of the Antiviral Activity of a Dendrimeric Peptide of Formula (VII) Containing ROD and DOE Motifs by Immunocytochemistry Dendrimic peptide of formula (VII):

[[(HRGDVFT)$_2$-Lys][(NDGECHV)$_2$-Lys]]-Lys-β-Ala-NH$_2$

To set up the assay, cells were seeded in 96-well plates and, once 80% confluence was achieved, were pre-treated for 1 with increasing concentrations of the dendrimeric peptide of formula (VII) and incubated at 37° C. Cells were then washed with medium and infected with the pre-activated virus (5 µg/ml tripsin for 30 minutes at 37° C.) in the presence of the peptide. After incubation cells were washed with medium and incubated in medium containing 0.5 µg/ml tripsin at 37° C. for 20 hours. The infected cells were visualised through an immunoperoxidase assay, using murine monoclonal antibodies specific for the capsidic protein VP6 of the rotavirus (Abcam) and the kit "UltraTech HRP Streptavidin-Biotin detection system" (Beckman Coulter). The infected cells were counted by observation under the optical microscope and the percentage of infection calculated by comparison of treated with non-treated cells. The dendrimeric peptide of formula (VII) inhibited rotavirus infection with an IC$_{50}$ of 3.6 µM.

Example 4a

Evaluation of the Synthetic Peptide SEQ ID NO: 1 by MALDI-TOF Mass Spectrometry and Instrumental Limit of Detection (LOD)

The experiments were performed on the peptide SEQ ID NO: 1 having the following amino acid sequence QNDGECHVIDDSHRGDVFTQ and a theoretical molecular mass of 2270.96 Da.

The peptide SEQ ID NO: 1 was dissolved in ultra pure H$_2$O to obtain a final concentration of 10 mg/ml. Dilutions from 1:10 to 1:10,000 were obtained. All concentrations were tested by MALDI-TOF analyses. 0.5 µl of samples from dilutions 1:10, 1:100, 1:1,000, 1:10,000 were spotted onto a MALDI target plate and left to dry at RT. 0.5 µl of α-cyano-4-hydroxy-cinnamic acid in 30% acetonitrile, 0.1% TFA (HCCA matrix solution) were added to each sample and left to dry under vacuum. Spectra were obtained using a Bruker Ultraflex II MALDI-TOF/TOF mass spectrometer (Bruker Daltonics) in reflectron and positive ion mode. External calibration was performed using "Peptide calibration standard" from Bruker Daltonics.

Figure 4:
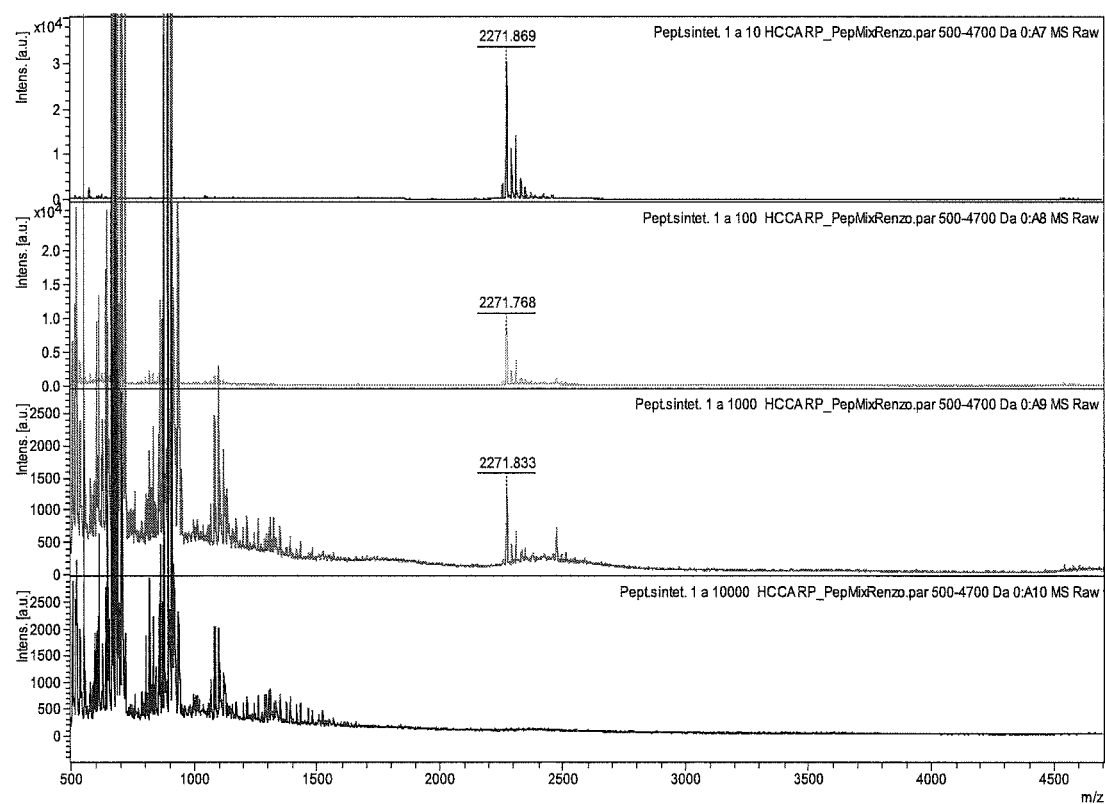
FIG. 4:
MALDI-TOF spectra of dilute solutions of SEQ ID NO: 1.

In FIG. 4 the MALDI-TOF spectra of the 4 dilutions are shown. The concentrations 1 mg/ml, 0.1 mg/ml and 0.01 mg/ml clearly show a good ion signal around 2272Da corresponding to the MW of the peptide SEQ ID NO: 1, added by one proton (from top to the bottom), whereas the most diluted sample didn't have a detectable signal. The LOD was establish to be at 0.01 mg/ml.

Example 4b

Kinetics of the Tryptic Activity on the SEQ ID NO: 1 Peptide

Figure 5:
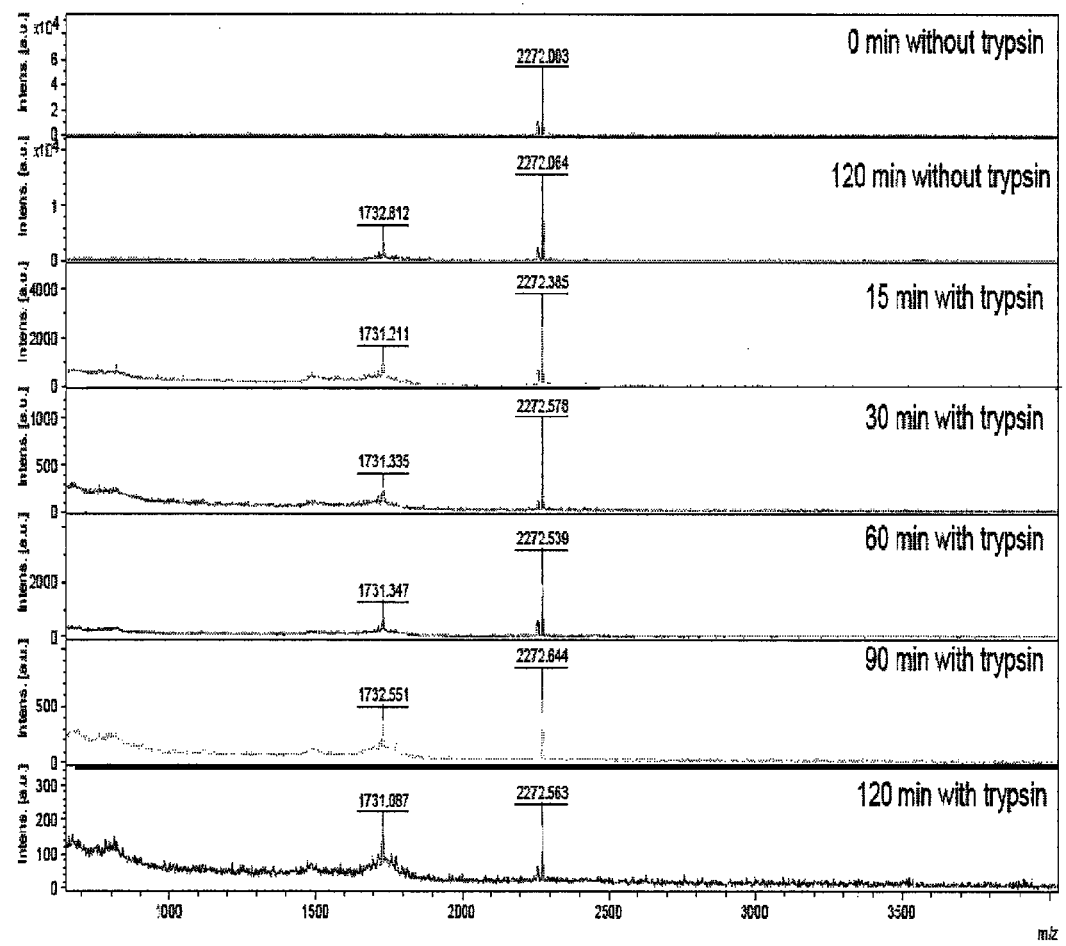
FIG. 5:
MALDI-TOF spectra of solutions of SEQ ID NO: 1 and trypsin at different times of digestion.

To evaluate the digestibility of the SEQ ID NO: 1 peptide with trypsin, 8 µl of a 0.2 µg/µl solution (25 mM NH$_4$HCO$_3$) of modified porcine trypsin (Promega) were added to 150 µl of the 10 mg/ml peptide solution ((25 mM NH$_4$HCO$_3$) enzyme to protein ratio 1:100). The sample was incubated at 37° C. and 0.5 µl were collected at different time of digestion: 5', 15', 30', 60' 90' 120'. Each samples was spotted on MALDI target and spectra were collected as already described in Example 4a. In FIG. 5 the time course experiment evaluated by MALDI TOF analyses is shown.

As shown in FIG. 5 the trypsin digestion didn't affect the integrity of the synthetic peptide. The signal at around 2272 Da is still present after 120' of incubation.

The subject-matter of the following items is also comprised by the present invention:

1. A peptidic compound having a length of up to 50 amino acids comprising an amino acid sequence represented by the general formula (I)

$$Z_n\text{-DGE-W}_m\text{-RGD-Z}_{r'} \qquad \text{formula (I)}$$

or a salt thereof, wherein
each of Z, Z' and W is an amino acid residue, particularly an α-amino carboxylic acid residue,
n is a number from 0 to 12, particularly from 1 to 6 and more particularly from 1 to 2, and
m is a number from 0 to 12, particularly from 1 to 10 and more particularly from 5-8, and
r is a number from 0 to 20, particularly from 1 to 12 and more particularly from 1 to 4, and wherein
D is an amino acid residue with an aspartic acid side chain, preferably L-aspartic acid, G is an amino acid residue with a glycine side chain,
E is an amino acid residue with a glutamic acid side chain, preferably L-glutamic acid, and
R is an amino acid residue with an arginine side chain, particularly L-arginine;
and wherein the peptidic compound of formula (I) may comprise L- and/or O-amino residues, preferably L-amino acid residues.

2. The peptidic compound of item 1, wherein the amino acid sequence is represented by the general formula (Ia):

$$([Y_1]_{n1}\text{-}[Y_2]_{n2}\text{-}DGE\text{-}[Y_3]_{n3}\text{-}[Y_4]_{n4}\text{-}[Y_5]_{n5})\text{-}W'\text{-}([X_1]_{m1}\text{-}X_2\text{-}RGD\text{-}X_3\text{-}X_4\text{-}X_5) \quad \text{formula (Ia)}$$

or a salt thereof, wherein
$Y_1$, $Y_2$ and $Y_3$ are independently amino acid residues with a neutral polar side chain, preferably with a serine (S), asparagine (N), cysteine (C), glutamine (Q), tyrosine (Y) or threonine (T) side chain,
$Y_4$ is an amino acid residue with a positively charged side chain, preferably with a histidine (H), arginine (R) or lysine (K) side chain,
$Y_5$ is an amino acid residue with a neutral non-polar side chain, preferably with a phenylalanine (F), valine (V), alanine (A), glycine (G), isoleucine (I), leucine (L), methionine (M), proline (P) or tryptophan (W) side chain,
D is an amino acid residue with an aspartic acid side chain, preferably L-aspartic acid,
G is an amino acid residue with a glycine side chain,
E is an amino acid residue with a glutamic acid side chain, preferably L-glutamic acid,
$n_1$, $n_4$ and $n_5$ are independently 0 or 1,
$n_2$ and $n_3$ are 0 or 1, with the provision that at least one of $n_2$ and $n_3$ is 1,
$X_1$ and $X_5$ are independently amino acid residues with a neutral polar side chain, preferably with a serine (S), asparagine (N), cysteine (C), glutamine (Q), tyrosine (Y) or threonine (T) side chain,
$X_2$ is an amino acid residue with a positively charged side chain, preferably with a histidine (H), arginine (R) or lysine (K) side chain,
$X_3$ and $X_4$ are independently amino acid residues with a neutral non-polar side chain, preferably with a phenylalanine (F), valine (V), alanine (A), glycine (G), isoleucine (I), leucine (L), methionine (M), proline (P) or tryptophan (W) side chain,
R is an amino acid residue with an arginine side chain, particularly L-arginine,
G is an amino acid residue with a glycine side chain,
D is an amino acid residue with an aspartic acid side chain, preferably L-aspartic acid, and
$m_1$ is 0 or 1,
and
W' is a covalent chemical bond or a linker group, preferably a peptidic linker group, comprising 1 to 10 amino acid residues, preferably 1 to 5, more preferably 1 to 3 amino acid residues and wherein the peptidic compound of formula Ia may comprise L- and/or O-amino acid residues, preferably L-amino acid residues.

3. The peptidic compound of item 1 or 2 comprising the amino acid sequence

```
                                            (SEQ ID NO: 1)
         Q-N-DGE-C-H-V-I-D-D-S-H-RGD-V-F-T-Q, (SEQ ID NO: 2)
         N-DGE-C-H-V-I-D-D-S-H-RGD-V-F-T-Q, (SEQ ID NO: 7)
         N-N-DGE-C-H-V-I-D-D-S-H-RGD-V-F-T-Q (SEQ ID NO: 8)
         Q-N-DGE-C-H-V-I-D-D-S-H-RGD-V-F-S-Q
    or
                                            (SEQ ID NO: 9)
         Q-N-DGE-C-H-V-I-D-D-S-H-RGD-V-F-Q-T.
``` wherein the amino acid residues are as defined in item 1, preferably L-amino acid residues.

4. A peptidic compound having a length of up to 50 amino acids comprising an amino acid sequence represented by the general formula (II)

$$[Y_1]_{n1}\text{-}[Y_2]_{n2}\text{-}DGE\text{-}[Y_3]_{n3}\text{-}[Y_4]_{n4}\text{-}[Y_5]_{n5} \quad \text{formula (II)}$$

or a salt thereof, wherein
$Y_1$, $Y_2$ and $Y_3$ are independently amino acid residues with a neutral polar side chain, preferably with a serine (S), asparagine (N), cysteine (C), glutamine (Q), tyrosine (Y) or threonine (T) side chain,
$Y_4$ is an amino acid residue with a positively charged side chain, preferably with a histidine (H), arginine (R) or lysine (K) side chain,
$Y_5$ is an amino acid residue with a neutral non-polar side chain, preferably with a phenylalanine (F), valine (V), alanine (A), glycine (G), isoleucine (I), leucine (L), methionine (M), proline (P) or tryptophan (W) side chain,
D is an amino acid residue with an aspartic acid side chain, preferably L-aspartic acid,
G is an amino acid residue with a glycine side chain,
E is an amino acid residue with a glutamic acid side chain, preferably L-glutamic acid,
$n_1$, $n_4$ and $n_5$ are independently 0 or 1,
$n_2$ and $n_3$ are 0 or 1, with the provision that at least one of $n_2$ and $n_3$ is 1, and
wherein the peptidic compound of formula (II) may comprise L- and/or D-amino acid residues, preferably L-amino acid residues.

5. The peptide compound of item 4 comprising the amino acid sequence

```
                                            (SEQ ID NO: 3)
                    Q-N-DGE-C-H-V
    or
                                            (SEQ ID NO: 4)
                    N-DGE-C-H-V,
``` wherein the amino acid residues are as defined in item 4, preferably L-amino acid residues.

6. A peptidic compound having a length of up to 50 amino acids comprising an amino acid sequence represented by the general formula (III)

$$[X_1]_{n1}\text{-}X_2\text{-}RGD\text{-}X_3\text{-}X_4\text{-}X_5 \quad \text{formula (III)}$$

or a salt thereof, wherein
$X_1$ and $X_5$ are independently amino acid residues with a neutral polar side chain, preferably with a serine (S), asparagine (N), cysteine (C), glutamine (Q), tyrosine (Y) or threonine (T) side chain,
$X_2$ is an amino acid residue with a positively charged side chain, preferably with a histidine (H), arginine (R) or lysine (K) side chain, $X_3$ and $X_4$ are independently amino acid residues with a neutral non-polar side chain, preferably with a phenylalanine (F), valine (V), alanine (A), glycine (G), isoleucine (I), leucine (L), methionine (M), proline (P) or tryptophan (W) side chain, R is an amino acid residue with an arginine side chain, particularly L-arginine, G is an amino acid residue with a glycine side chain, D is an amino acid residue with an aspartic acid side chain, preferably L-aspartic acid, and $m_1$ is 0 or 1, and wherein the peptidic compound of formula III may comprise L- and/or D-amino acid residues, preferably L-amino acid residues.

7. The peptidic compound of item 6 comprising the amino acid sequence

S-H-RGD-V-F-T   (SEQ ID NO: 5)

or

H-RGD-V-F-T,   (SEQ ID NO: 6)

wherein the amino acid residues are as defined in item 6, preferably L-amino acid residues.

8. The peptidic compound of any one of items 1-7 in combination with a further active agent, e.g. a further antiviral peptidic compound as defined in any one of items 1-7.

9. The peptidic compound of any one of items 1-8, which is a linear or cyclic peptide.

10. The peptidic compound of any one of items 1-9, wherein
   (i) the peptidic compound of formula I has a length of from at least 6, 8, 10, 12, 14, 16, 19 or 20 amino acid residues, preferably of at least 19 or 20 amino acid residues,
   (ii) the peptidic compound of formula Ia has a length of from at least 11, 12, 13, 14, 15, 16, 17, 18, 19 or 20 amino acid residues, preferably of at least 19 or 20 amino acid residues,
   (iii) the peptidic compound of formula II has a length of from at least 4, 6, 7, 8 or 10 amino acid residues, preferably of at least 7 or 8 amino acid residues, and
   (iv) the peptidic compound of formula III has a length of from at least 7, 8, 10, 12 or 14 amino acid residues, preferably of at least 7 or 8 amino acid residues.

11. The peptidic compound of any one of items 1-9, which has a length of up to 45, 30, 35, 20 or 15 amino acid residues.

12. The peptidic compound of any one of items 1-11, which is a naturally occurring amino acid sequence portion of equine lactadherin, particularly of horse and donkey lactadherin.

13. A multimeric compound comprising as units a plurality of peptidic compounds as defined in any one of items 1-12.

14. The multimeric compound of item 13 which has a linear or a branched, particularly a dendritic structure.

15. The multimeric compound of item 13 or 14, which is selected from:

(i) $P_c\text{-}(J^1\text{-}P_c)_m J^1\text{-}(P_c)_{m'}$   (IVa)

wherein $P_c$ is a peptidic compound as defined in any one of items 1-12, $J^1$ is a covalent bond or a bifunctional linker, e.g. a dialcohol such as propylene glycol, a dicarboxylic acid such as succinic acid, a diamine such as ethylene diamine, an amino acid, a hydroxy carboxylic acid, or or a diisocyanate, and m is 0 or a positive whole number, and m' is 0 or 1, (ii) $[[(P_c)_{n1} J^{1'}]_{n2}] J^2$   (IVb)

wherein $P_c$ is a peptidic compound as defined in any one of items 1-12, $J^{1'}$ is in each case independently a linker having a functionality of at least 3, e.g. a trifunctional amino acid such as lysine, ornithine, nor-lysine, aminoalanine, aspartic acid or glutamic acid, and $J^2$ is a linker having a functionality of at least 2, and $n_1$ and $n_2$ in each case independently are a whole number of at least 2, preferably 2, 3 or 4, more preferably 2, (iii) $\{[[(P_c)_{n1} J^{1'}]_{n2} J^{2'}\}_{n3} J^3$   (IVc)

wherein $P_c$ is a peptidic compound as defined in any one of items 1-12, $J^{1'}$ and $J^{2'}$ are in each case independent linkers having a functionality of at least 3, e.g. a trifunctional amino acid such as lysine, ornithine, norlysine, aminoalanine, aspartic acid or glutamic acid, $J^3$ is a linker having a functionality of at least 2 and $n_1$, $n_2$ and $n_3$ are in each case independently whole numbers of at least 2, preferably 2, 3 or 4, more preferably 2.

16. The multimeric compound of any one of items 13-15 in combination with a further active agent, e.g. a further antiviral peptidic compound of any one of items 1-12 or a further antiviral multimeric compound of any one of items 13-15.

17. The compound of any one of items 1-16, which is a modified compound, e.g. an N-terminally and/or C-terminally modified compound.

18. The compound of any one of items 1-17 for use as a medicament.

19. The compound of any one of items 1-17 for use as a medicament for the prevention and/or treatment of a viral infection, particularly of an integrin-using viral infection.

20. The compound of item 19 for the prevention and/or treatment of a rotavirus, herpes virus, coxsackie virus, metapneumovirus, West Nile virus, and/or foot-and-mouth disease virus infection, particularly a rotavirus infection.

21. A composition for medical use comprising at least one compound of any one of items 1-17 together with a pharmaceutically acceptable excipients, carriers and/or diluents.

22. The composition of item 21 for oral administration.

23. The composition of items 21 and 22, which is in a powdered form.

24. The composition of any one of items 21-23 for the prevention and/or treatment of a viral infection, in particular of an integrin-using viral infection.

25. The composition of any one of items 21-23 for administration to children and/or newborns.

26. The compound of any one of items 1-17 for use as a food additive, in particular as additive for children and/or newborns food stuff, e.g. powdered milk.

The invention claimed is:

1. A peptidic compound having a length of up to 50 amino acids and having anti-viral activity, comprising an amino acid sequence represented by the general formula (I)

$$Z_n\text{-DGE-}B_m\text{-RGD-}Z_{r}'\qquad\text{formula (I)}$$

or a salt thereof, wherein
each of Z, Z' and B is an amino acid residue, particularly an α-amino carboxylic acid residue,
n is a number from 1 to 12, and
m is a number from 0 to 12, and
r is a number from 0 to 20, and wherein
D is an amino acid residue with an aspartic acid side chain, preferably L-aspartic acid,
G is an amino acid residue with a glycine side chain,
E is an amino acid residue with a glutamic acid side chain, preferably L-glutamic acid, and
R is an amino acid residue with an arginine side chain, particularly L-arginine;
and wherein the peptidic compound of formula (I) may comprise L- and/or D-amino residues, preferably L-amino acid residues.

2. The peptidic compound of claim 1, wherein the amino acid sequence is represented by the general formula (Ia)

$$([Y_1]_{n1}\text{-}[Y_2]_{n2}\text{-}DGE\text{-}[Y_3]_{n3}\text{-}[Y_4]_{n4}\text{-}[Y_5]_{n5})\text{-}B'\text{-}([X_1]_{m1}\text{-}X_2\text{-}RGD\text{-}X_3\text{-}X_4\text{-}X_5) \quad \text{formula (Ia)}$$

or a salt thereof, wherein $Y_1$, $Y_2$ and $Y_3$ are independently amino acid residues with a neutral polar side chain, preferably with a serine (S), asparagine (N), cysteine (C), glutamine (Q), tyrosine (Y) or threonine (T) side chain, $Y_4$ is an amino acid residue with a positively charged side chain, preferably with a histidine (H), arginine (R) or lysine (K) side chain, $Y_5$ is an amino acid residue with a neutral non-polar side chain, preferably with a phenylalanine (F), valine (V), alanine (A), glycine (G), isoleucine (I), leucine (L), methionine (M), proline (P) or tryptophan (W) side chain, D is an amino acid residue with an aspartic acid side chain, preferably L-aspartic acid, G is an amino acid residue with a glycine side chain, E is an amino acid residue with a glutamic acid side chain, preferably L-glutamic acid, $n_1$, $n_4$ and $n_5$ are independently 0 or 1, $n_2$ and $n_3$ are 0 or 1, with the provision that at least one of $n_2$ and $n_3$ is 1, $X_1$ and $X_5$ are independently amino acid residues with a neutral polar side chain, preferably with a serine (S), asparagine (N), cysteine (C), glutamine (Q), tyrosine (Y) or threonine (T) side chain, $X_2$ is an amino acid residue with a positively charged side chain, preferably with a histidine (H), arginine (R) or lysine (K) side chain, $X_3$ and $X_4$ are independently amino acid residues with a neutral non-polar side chain, preferably with a phenylalanine (F), valine (V), alanine (A), glycine (G), isoleucine (I), leucine (L), methionine (M), proline (P) or tryptophan (W) side chain, R is an amino acid residue with an arginine side chain, particularly L-arginine, G is an amino acid residue with a glycine side chain, D is an amino acid residue with an aspartic acid side chain, preferably L-aspartic acid, and $m_1$ is 0 or 1, and B' is a covalent chemical bond or a linker group, preferably a peptidic linker group, comprising 1 to 10 amino acid residues, and wherein the peptidic compound of formula Ia may comprise L- and/or D-amino acid residues, preferably L-amino acid residues.

3. The peptidic compound of claim 1 comprising the amino acid sequence (SEQ ID NO: 1)
Q-N-DGE-C-H-V-I-D-D-S-H-RGD-V-F-T-Q, (SEQ ID NO: 2)
N-DGE-C-H-V-I-D-D-S-H-RGD-V-F-T-Q, (SEQ ID NO: 7)
N-N-DGE-C-H-V-I-D-D-S-H-RGD-V-F-T-Q (SEQ ID NO: 8)
Q-N-DGE-C-H-V-I-D-D-S-H-RGD-V-F-S-Q
or (SEQ ID NO: 9)
Q-N-DGE-C-H-V-I-D-D-S-H-RGD-V-F-Q-T, wherein the amino acid residues are as defined in claim 1, preferably L-amino acid residues.

4. A peptidic compound having a length of up to 50 amino acids comprising an amino acid sequence represented by the general formula (II)

$$[Y_1]_{n1}\text{-}[Y_2]_{n2}\text{-}DGE\text{-}[Y_3]_{n3}\text{-}[Y_4]_{n4}\text{-}[Y_5]_{n5} \quad \text{formula (II)}$$

or a salt thereof, wherein $Y_1$, $Y_2$ and $Y_3$ are independently amino acid residues with a neutral polar side chain, preferably with a serine (S), asparagine (N), cysteine (C), glutamine (Q), tyrosine (Y) or threonine (T) side chain, $Y_4$ is an amino acid residue with a positively charged side chain, preferably with a histidine (H), arginine (R) or lysine (K) side chain, $Y_5$ is an amino acid residue with a neutral non-polar side chain, preferably with a phenylalanine (F), valine (V), alanine (A), glycine (G), isoleucine (I), leucine (L), methionine (M), proline (P) or tryptophan (W) side chain, D is an amino acid residue with an aspartic acid side chain, preferably L-aspartic acid, G is an amino acid residue with a glycine side chain, E is an amino acid residue with a glutamic acid side chain, preferably L-glutamic acid, $n_1$, $n_4$ and $n_5$ are independently 0 or 1, $n_2$ and $n_3$ are 0 or 1, with the provision that at least one of $n_2$ and $n_3$ is 1, and wherein the peptidic compound of formula (II) may comprise L- and/or D-amino acid residues, preferably L-amino acid residues.

5. The peptide compound of claim 4 comprising the amino acid sequence (SEQ ID NO: 3)
Q-N-DGE-C-H-V
or (SEQ ID NO: 4)
N-DGE-C-H-V, wherein the amino acid residues are as defined in claim 4, preferably L-amino acid residues.

6. A peptidic compound having a length of up to 50 amino acids comprising an amino acid sequence represented by the general formula (III)

$$[X_1]_{m1}\text{-}X_2\text{-}RGD\text{-}X_3\text{-}X_4\text{-}X_5 \quad \text{formula (III)}$$

or a salt thereof, wherein $X_1$ and $X_5$ are independently amino acid residues with a neutral polar side chain, preferably with a serine (S), asparagine (N), cysteine (C), glutamine (Q), tyrosine (Y) or threonine (T) side chain, $X_2$ is an amino acid residue with a positively charged side chain, preferably with a histidine (H), arginine (R) or lysine (K) side chain, $X_3$ and $X_4$ are independently amino acid residues with a neutral non-polar side chain, preferably with a phenylalanine (F), valine (V), alanine (A), glycine (G), isoleucine (I), leucine (L), methionine (M), proline (P) or tryptophan (W) side chain, R is an amino acid residue with an arginine side chain, particularly L-arginine, G is an amino acid residue with a glycine side chain, D is an amino acid residue with an aspartic acid side chain, preferably L-aspartic acid, and m₁ is 1, and
wherein the peptidic compound of formula III may comprise L- and/or D-amino acid residues, preferably L-amino acid residues.

7. The peptidic compound of claim 6 comprising the amino acid sequence (SEQ ID NO: 5)
S-H-RGD-V-F-T wherein the amino acid residues are as defined in claim 6, preferably L-amino acid residues.

8. The peptidic compound of claim 1 in combination with a further active agent.

9. The peptidic compound of claim 1, wherein
(i) the peptidic compound of formula I has a length selected from the group consisting of 6, 8, 10, 12, 14, 16, 19 and 20 amino acid residues.

10. A multimeric compound comprising as units a plurality of peptidic compounds as defined in claim 1 which has a linear or a branched, structure.

11. The multimeric compound of claim 10, which is selected from:

(i) $P_c\text{-}(J^1\text{-}P_c)_m\text{-}J^1\text{-}(P_c)_{m'}$ (IVa)
wherein $P_c$ is a said peptidic compound,
$J^1$ is a covalent bond or a bifunctional linker, e.g. a dialcohol such as propylene glycol, a dicarboxylic acid such as succinic acid, a diamine such as ethylene diamine, an amino acid, a hydroxy carboxylic acid, or or a diisocyanate, and m is 0 or a positive whole number, and m' is 0 or 1, (ii) $[[(P_c)_{n1}J^{1'}]_{n2}]J^2$ (IVb)
wherein $P_c$ is a said peptidic compound,
$J^{1'}$ is in each case independently a linker having a functionality of at least 3, e.g. a trifunctional amino acid such as lysine, ornithine, nor-lysine, aminoalanine, aspartic acid or glutamic acid, and
$J^2$ is a linker having a functionality of at least 2, and
$n_1$ and $n_2$ in each case independently are a whole number of at least 2, preferably 2, 3 or 4, more preferably 2, (iii) $\{[[(P_c)_{n1}J^{1'}]_{n2}J^{2'}\}_{n3}J^3$ (IVc)
wherein $P_c$ is a said peptidic compound,
$J^{1'}$ and $J^{2'}$ are in each case independent linkers having a functionality of at least 3, e.g. a trifunctional amino acid such as lysine, ornithine, norlysine, aminoalanine, aspartic acid or glutamic acid,
$J^3$ is a linker having a functionality of at least 2 and
$n_1$, $n_2$ and $n_3$ are in each case independently whole numbers of at least 2.

12. The multimeric compound of claim 10 in combination with a further antiviral active agent.

13. A pharmaceutical comprising at least one compound of claim 1 together with at least one pharmaceutically acceptable excipient, carrier and/or diluent.

14. The composition of claim 13 in a form for oral administration.

15. A food composition comprising the compound of claim 1 and a food.

16. The multimeric compound of claim 10 in combination with a further antiviral active agent.

17. The peptidic compound of claim 1, wherein n is a number from 1 to 6.

18. The peptidic compound of claim 17, wherein n is a number from 1 to 2.

19. The peptidic compound of claim 1, wherein m is a number from 1 to 10.

20. The peptidic compound of claim 19, wherein m is a number from 5 to 8.

21. The peptidic compound of claim 1, wherein r is a number from 1 to 12.

22. The peptidic compound of claim 21, wherein r is a number from 1 to 4.

23. The peptidic compound of claim 2, wherein B' comprises 1 to 5 amino acid residues.

24. The peptidic compound of claim 23, wherein B' comprises 1 to 3 amino acid residues.

25. The peptidic compound of claim 11, wherein $n_1$, $n_2$ and $n_3$ are whole numbers selected from the group consisting of 2, 3 and 4.

26. The peptidic compound of claim 25, wherein $n_1$, $n_2$ and $n_3$ are whole numbers equalling 2.

27. The peptidic compound of claim 8, wherein said further active agent is an antiviral peptidic compound.

28. The multimeric compound of claim 16, wherein said antiviral active agent is an antiviral multimeric compound as defined in claim 10.

29. The peptidic compound of claim 9, wherein said length is 19 amino acid residues.

30. The peptidic compound of claim 9, wherein said length is 20 amino acid residues.

31. The peptidic compound of claim 2, wherein the peptidic compound of formula Ia has a length selected from the group consisting of 11, 12, 13, 14, 15, 16, 17, 18, 19, and 20 amino acid residues.

32. The peptidic compound of claim 31, wherein said length is 19 amino acid residues.

33. The peptidic compound of claim 31, wherein said length is 20 amino acid residues.

34. The peptidic compound of claim 4, wherein the peptidic compound of formula II has a length selected from the group consisting of 4, 6, 7, 8, and 10 amino acid residues.

35. The peptidic compound of claim 34, wherein said length is 7 amino acid residues.

36. The peptidic compound of claim 34, wherein said length is 8 amino acid residues.

37. The peptidic compound of claim 6, wherein the peptidic compound of formula III has a length selected from the group consisting of 7, 8, 10, 12, and 14 amino acid residues.

38. The peptidic compound of claim 37, wherein said length is 7 amino acid residues.

39. The peptidic compound of claim 37, wherein said length is 8 amino acid residues.

40. The multimeric compound of claim 10, wherein the branched structure is a dendritic structure.

41. The composition of claim 14, wherein said form is a powdered form.

42. The food composition of claim 15, wherein said food is child and/or newborn food.

43. The food composition of claim 42, wherein said child and/or newborn food is powdered milk.

44. The multimeric compound of claim 12, wherein said antiviral active agent is an antiviral peptidic compound.

* * * * *

SEQUENCE LISTING

<160> NUMBER OF SEQ ID NOS: 24

<210> SEQ ID NO 1

```
<211> LENGTH: 20
<212> TYPE: PRT
<213> ORGANISM: Artificial Sequence
<220> FEATURE:
<223> OTHER INFORMATION: Specific examples of peptidic compounds of
      formula I and /or formula Ia

<400> SEQUENCE: 1

Gln Asn Asp Gly Glu Cys His Val Ile Asp Asp Ser His Arg Gly Asp
1               5                   10                  15

Val Phe Thr Gln
            20

<210> SEQ ID NO 2
<211> LENGTH: 19
<212> TYPE: PRT
<213> ORGANISM: Artificial Sequence
<220> FEATURE:
<223> OTHER INFORMATION: Specific examples of peptidic compounds of
      formula I and /or formula Ia

<400> SEQUENCE: 2

Asn Asp Gly Glu Cys His Val Ile Asp Asp Ser His Arg Gly Asp Val
1               5                   10                  15

Phe Thr Gln

<210> SEQ ID NO 3
<211> LENGTH: 8
<212> TYPE: PRT
<213> ORGANISM: Artificial Sequence
<220> FEATURE:
<223> OTHER INFORMATION: Specific examples of peptidic compounds of
      formula II

<400> SEQUENCE: 3

Gln Asn Asp Gly Glu Cys His Val
1               5

<210> SEQ ID NO 4
<211> LENGTH: 7
<212> TYPE: PRT
<213> ORGANISM: Artificial Sequence
<220> FEATURE:
<223> OTHER INFORMATION: Specific examples of peptidic compounds of
      formula II

<400> SEQUENCE: 4

Asn Asp Gly Glu Cys His Val
1               5

<210> SEQ ID NO 5
<211> LENGTH: 8
<212> TYPE: PRT
<213> ORGANISM: Artificial Sequence
<220> FEATURE:
<223> OTHER INFORMATION: Specific examples of the peptidic compound of
      formula III

<400> SEQUENCE: 5

Ser His Arg Gly Asp Val Phe Thr
1               5

<210> SEQ ID NO 6
<211> LENGTH: 7
<212> TYPE: PRT
<213> ORGANISM: Artificial Sequence
<220> FEATURE:
<223> OTHER INFORMATION: Specific examples of the peptidic compound of
``` formula III

<400> SEQUENCE: 6

His Arg Gly Asp Val Phe Thr
1               5

<210> SEQ ID NO 7
<211> LENGTH: 20
<212> TYPE: PRT
<213> ORGANISM: Artificial Sequence
<220> FEATURE:
<223> OTHER INFORMATION: Preferred examples of peptidic compounds of
      formula I and/or formula Ia

<400> SEQUENCE: 7

Asn Asn Asp Gly Glu Cys His Val Ile Asp Asp Ser His Arg Gly Asp
1               5                   10                  15

Val Phe Thr Gln
            20

<210> SEQ ID NO 8
<211> LENGTH: 20
<212> TYPE: PRT
<213> ORGANISM: Artificial Sequence
<220> FEATURE:
<223> OTHER INFORMATION: Preferred examples of peptidic compounds of
      formula I and/or formula Ia

<400> SEQUENCE: 8

Gln Asn Asp Gly Glu Cys His Val Ile Asp Asp Ser His Arg Gly Asp
1               5                   10                  15

Val Phe Ser Gln
            20

<210> SEQ ID NO 9
<211> LENGTH: 20
<212> TYPE: PRT
<213> ORGANISM: Artificial Sequence
<220> FEATURE:
<223> OTHER INFORMATION: Preferred examples of peptidic compounds of
      formula I and/or formula Ia

<400> SEQUENCE: 9

Gln Asn Asp Gly Glu Cys His Val Ile Asp Asp Ser His Arg Gly Asp
1               5                   10                  15

Val Phe Gln Thr
            20

<210> SEQ ID NO 10
<211> LENGTH: 20
<212> TYPE: PRT
<213> ORGANISM: Artificial Sequence
<220> FEATURE:
<223> OTHER INFORMATION: Modification of the DGE-motif and RGD-motif
      (DGE -> AGE mutation, RGD -> RGE mutation)

<400> SEQUENCE: 10

Gln Asn Ala Gly Glu Cys His Val Ile Asp Asp Ser His Arg Gly Glu
1               5                   10                  15

Val Phe Thr Gln
            20

<210> SEQ ID NO 11
<211> LENGTH: 20
<212> TYPE: PRT
<213> ORGANISM: Artificial Sequence

```
<220> FEATURE:
<223> OTHER INFORMATION: Modification of the amino acid residue X2
      according to formula Ia to an amino acid residue with an aspartic
      acid side chain (D).

<400> SEQUENCE: 11

Gln Asn Asp Gly Glu Cys His Val Ile Asp Asp Ser Asp Arg Gly Asp
1               5                   10                  15

Val Phe Thr Gln
            20

<210> SEQ ID NO 12
<211> LENGTH: 8
<212> TYPE: PRT
<213> ORGANISM: Artificial Sequence
<220> FEATURE:
<223> OTHER INFORMATION: Peptidic compound based on the sequence
      portion of the naturally occurring equine lactadherin sequence

<400> SEQUENCE: 12

Cys His Val Ile Asp Asp Ser His
1               5

<210> SEQ ID NO 13
<211> LENGTH: 12
<212> TYPE: PRT
<213> ORGANISM: Artificial Sequence
<220> FEATURE:
<223> OTHER INFORMATION: Peptidic compound based on the sequence
      portion of the naturally occurring equine lactadherin sequence

<400> SEQUENCE: 13

Ala Ser Gly Pro Cys Phe Pro Asn Pro Cys Gln Asn
1               5                   10

<210> SEQ ID NO 14
<211> LENGTH: 19
<212> TYPE: PRT
<213> ORGANISM: Artificial Sequence
<220> FEATURE:
<223> OTHER INFORMATION: Peptidic compound based on the sequence
      portion of the naturally occurring equine lactadherin sequence

<400> SEQUENCE: 14

Val Phe Thr Gln Tyr Ile Cys Ser Cys Pro Arg Gly Tyr Thr Gly Thr
1               5                   10                  15

His Cys Glu

<210> SEQ ID NO 15
<211> LENGTH: 8
<212> TYPE: PRT
<213> ORGANISM: Artificial Sequence
<220> FEATURE:
<223> OTHER INFORMATION: Mutated peptidic compound (RGD -> RGE mutation)

<400> SEQUENCE: 15

Ser His Arg Gly Glu Val Phe Thr
1               5

<210> SEQ ID NO 16
<211> LENGTH: 8
<212> TYPE: PRT
<213> ORGANISM: Artificial Sequence
<220> FEATURE:
<223> OTHER INFORMATION: Mutated peptidic compound (DGE -> AGE mutation)

<400> SEQUENCE: 16
```

```
Gln Asn Ala Gly Glu Cys His Val
1               5

<210> SEQ ID NO 17
<211> LENGTH: 8
<212> TYPE: PRT
<213> ORGANISM: Artificial Sequence
<220> FEATURE:
<223> OTHER INFORMATION: Peptidic compound derived from bovine
      lactadherin sequence

<400> SEQUENCE: 17

Ser His Arg Gly Asp Val Phe Ile
1               5

<210> SEQ ID NO 18
<211> LENGTH: 8
<212> TYPE: PRT
<213> ORGANISM: Artificial Sequence
<220> FEATURE:
<223> OTHER INFORMATION: Peptidic compound derived from human
      lactadherin sequence

<400> SEQUENCE: 18

Glu Val Arg Gly Asp Val Phe Pro
1               5

<210> SEQ ID NO 19
<211> LENGTH: 4
<212> TYPE: PRT
<213> ORGANISM: Artificial Sequence
<220> FEATURE:
<223> OTHER INFORMATION: Control peptide

<400> SEQUENCE: 19

Asp Gly Glu Ala
1

<210> SEQ ID NO 20
<211> LENGTH: 45
<212> TYPE: PRT
<213> ORGANISM: Equus asinus

<400> SEQUENCE: 20

Ala Ser Gly Pro Cys Phe Pro Asn Pro Cys Gln Asn Asp Gly Glu Cys
1               5                   10                  15

His Val Ile Asp Asp Ser His Arg Gly Asp Val Phe Thr Gln Tyr Ile
            20                  25                  30

Cys Ser Cys Pro Arg Gly Tyr Thr Gly Thr His Cys Glu
        35                  40                  45

<210> SEQ ID NO 21
<211> LENGTH: 55
<212> TYPE: PRT
<213> ORGANISM: Equus sp.

<400> SEQUENCE: 21

Ala Ser Gly Cys Phe Pro Asn Pro Cys Gln Asn Asp Gly Glu Cys His
1               5                   10                  15

Val Ile Asp Asp Ser His Arg Gly Asp Val Phe Thr Gln Tyr Ile Cys
            20                  25                  30

Ser Cys Pro Arg Gly Tyr Thr Gly His Cys Glu Thr Thr Cys Ala Met
        35                  40                  45

Pro Leu Gly Met Glu Thr Gly
        50              55
```

<210> SEQ ID NO 22
<211> LENGTH: 120
<212> TYPE: PRT
<213> ORGANISM: Bos sp.

<400> SEQUENCE: 22

```
Ala Ser Gly Asp Phe Cys Asp Ser Ser Leu Cys Leu His Gly Gly Thr
1               5                   10                  15
Cys Leu Leu Asn Glu Asp Arg Thr Pro Pro Phe Tyr Cys Leu Cys Pro
            20                  25                  30
Glu Gly Phe Thr Gly Leu Leu Cys Asn Glu Thr Glu His Gly Pro Cys
        35                  40                  45
Phe Pro Asn Pro Cys His Asn Asp Ala Glu Cys Gln Val Thr Asp Asp
    50                  55                  60
Ser His Arg Gly Asp Val Phe Ile Gln Tyr Ile Cys Lys Cys Pro Leu
65                  70                  75                  80
Gly Tyr Val Gly Ile His Cys Glu Thr Thr Cys Thr Ser Pro Leu Gly
                85                  90                  95
Met Gln Thr Gly Ala Ile Ala Asp Ser Gln Ile Ser Ala Ser Ser Met
            100                 105                 110
His Leu Gly Phe Met Gly Leu Gln
        115                 120
```

<210> SEQ ID NO 23
<211> LENGTH: 60
<212> TYPE: PRT
<213> ORGANISM: Homo sapiens

<400> SEQUENCE: 23

```
Leu Asp Ile Cys Ser Lys Asn Pro Cys His Asn Gly Gly Leu Cys Glu
1               5                   10                  15
Glu Ile Ser Gln Glu Val Arg Gly Asp Val Phe Pro Ser Tyr Thr Cys
            20                  25                  30
Thr Cys Leu Lys Gly Tyr Ala Gly Asn His Cys Glu Thr Lys Cys Val
        35                  40                  45
Glu Pro Leu Gly Met Glu Asn Gly Asn Ile Ala Asn
    50                  55                  60
```

<210> SEQ ID NO 24
<211> LENGTH: 4
<212> TYPE: PRT
<213> ORGANISM: Artificial Sequence
<220> FEATURE:
<223> OTHER INFORMATION: integrin ligand peptide

<400> SEQUENCE: 24

```
Gly Pro Arg Pro
1
```